(12) United States Patent
Fukuoka et al.

(10) Patent No.: US 7,531,616 B2
(45) Date of Patent: May 12, 2009

(54) PROCESS FOR INDUSTRIAL PRODUCTION OF AN AROMATIC CARBONATE

(75) Inventors: Shinsuke Fukuoka, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 111 days.

(21) Appl. No.: 11/632,170

(22) PCT Filed: Jul. 12, 2005

(86) PCT No.: PCT/JP2005/012818

§ 371 (c)(1),
(2), (4) Date: Jan. 11, 2007

(87) PCT Pub. No.: WO2006/006588

PCT Pub. Date: Jan. 19, 2006

(65) Prior Publication Data

US 2007/0191623 A1    Aug. 16, 2007

(30) Foreign Application Priority Data

Jul. 14, 2004    (JP) .............................. 2004-207662

(51) Int. Cl.
*C08G 64/00* (2006.01)
*C08G 63/02* (2006.01)
(52) U.S. Cl. ....................... 528/196; 422/129; 422/131; 558/270; 558/274; 558/277; 528/198
(58) Field of Classification Search ................. 422/129, 422/131; 558/270, 274, 277; 528/196, 198
See application file for complete search history.

(56) References Cited

U.S. PATENT DOCUMENTS 5,210,268 A * 5/1993 Fukuoka et al. ............. 558/270

FOREIGN PATENT DOCUMENTS

| EP | 0 461 274 A1 | 12/1991 |
| EP | 1 762 559 A1 | 3/2007 |
| EP | 1 762 560 A1 | 3/2007 |
| WO | WO-2006/001256 A1 | 1/2006 |

* cited by examiner

*Primary Examiner*—Terressa M Boykin
(74) *Attorney, Agent, or Firm*—Birch, Stewart, Kolasch & Birch, LLP

(57) ABSTRACT

It is an object of the present invention to provide a specific process that enables aromatic carbonates to be produced with high selectivity and high productivity stably for a prolonged period of time on an industrial scale of not less than 1 ton per hour from a dialkyl carbonate and an aromatic monohydroxy compound using two continuous multi-stage distillation columns. Although there have been various proposals regarding processes for the production of aromatic carbonates by means of a reactive distillation method, these have all been on a small scale and short operating time laboratory level, and there have been no disclosures whatsoever on a specific process or apparatus enabling mass production on an industrial scale. According to the present invention, there are provided two specified continuous multi-stage distillation columns, and there is also provided a specific process that enables aromatic carbonates to be produced with high selectivity and high productivity stably for a prolonged period of time on an industrial scale of not less than 1 ton per hour from a dialkyl carbonate and an aromatic monohydroxy compound using a apparatus in which these two continuous multi-stage distillation columns are connected together.

33 Claims, 3 Drawing Sheets

US 7,531,616 B2

PROCESS FOR INDUSTRIAL PRODUCTION OF AN AROMATIC CARBONATE

TECHNICAL FIELD

The present invention relates to an industrial process for the production of an aromatic carbonate. More particularly, the present invention relates to an industrial process for the production of a large amount of an aromatic carbonate containing a diaryl carbonate as a main product, which is useful as a raw material of a transesterification method polycarbonate by subjecting a dialkyl carbonate and an aromatic monohydroxy compound to transesterification reaction in two continuous multi-stage distillation columns in each of which a catalyst is present.

BACKGROUND ART

An aromatic carbonates is important as a raw material for the production of aromatic polycarbonate which is the most widely used engineering plastic, without using toxic phosgene. As a process for producing an aromatic carbonate, a process of reacting an aromatic monohydroxy compound with phosgene has been known from long ago, and has also been the subject of a variety of studies in recent years. However, this process has the problem of using phosgene, and in addition chlorinated impurities that are difficult to separate out are present in the aromatic carbonate produced using this process, and hence the aromatic carbonate cannot be used as the raw material for the production of the aromatic polycarbonate. Because such chlorinated impurities markedly inhibit the polymerization reaction in the transesterification method which is carried out in the presence of an extremely small amount of a basic catalyst; for example, even if such chlorinated impurities are present in an amount of only 1 ppm, the polymerization hardly proceeds at all. To make the aromatic carbonate capable of being used as the raw material of polycarbonate of the transesterification method, troublesome multi-stage separation/purification processes such as enough washing with a dilute aqueous alkaline solution and hot water, oil/water separation, distillation and so on are thus required. Furthermore, the yield of the aromatic carbonate decreases due to hydrolysis loss during this separation/purification processes. Therefore, there are many problems in carrying out this method economically on an industrial scale.

On the other hand, a process for producing aromatic carbonates through transesterification reactions between a dialkyl carbonate and an aromatic monohydroxy compound is also known. However, such transesterification reactions are all equilibrium reactions. Since the equilibriums are biased extremely toward the original system and the reaction rates are slow, and hence there have been many difficulties in producing aromatic carbonates industrially in large amounts using this method. Several proposals have been made to improve on the above difficulties, but most of these have related to development of a catalyst to increase the reaction rate. Many metal compounds have been proposed as catalysts for this type of transesterification reaction. For example, Lewis acids such as a transition metal halide and Lewis acid-forming compounds (see Patent Documents 1: Japanese Patent Application Laid-Open No. 51-105032, Japanese Patent Application Laid-Open No. 56-123948, Japanese Patent Application Laid-Open No. 56-123949 (corresponding to West German Patent Application No. 2528412, British Patent No. 1499530, and U.S. Pat. No. 4,182,726), Japanese Patent Application Laid-Open No. 51-75044 (corresponding to West German Patent Application No. 2552907, and U.S. Pat. No. 4,045,464)), tin compounds such as an organo-tin alkoxide and an organo-tin oxides (see Patent Documents 2: Japanese Patent Application Laid-Open No. 54-48733 (corresponding to West German Patent Application No. 2736062), Japanese Patent Application Laid-Open No. 54-63023, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552,704), Japanese Patent Application Laid-Open No. 62-277345, Japanese Patent Application Laid-Open No. 1-265063, Japanese Patent Application Laid-Open No. 60-169444 (corresponding to U.S. Pat. No. 4,554,110), Japanese Patent Application Laid-Open No. 60-169445 (corresponding to U.S. Pat. No. 4,552, 704), Japanese Patent Application Laid-Open No. 62-277345, Japanese Patent Application Laid-Open No. 1-265063), salts and alkoxides of alkali metals and alkaline earth metals (see Patent Document 3: Japanese Patent Application Laid-Open No. 57-176932), lead compounds (see Patent Documents 4: Japanese Patent Application Laid-Open No. 57-176932, Japanese Patent Application Laid-Open No. 1-93560), complexes of metals such as copper, iron and zirconium (see Patent Document 5: Japanese Patent Application Laid-Open No. 57-183745), titanic acid esters (see Patent Documents 6: Japanese Patent Application Laid-Open No. 58-185536 (corresponding to U.S. Pat. No. 4,410,464), Japanese Patent Application Laid-Open No. 1-265062), mixtures of a Lewis acid and a protonic acid (see Patent Document 7: Japanese Patent Application Laid-Open No. 60-173016 (corresponding to U.S. Pat. No. 4,609,501)), compounds of Sc, Mo, Mn, Bi, Te or the like (see Patent Document 8: Japanese Patent Application Laid-Open No. 1-265064), ferric acetate (see Patent Document 9: Japanese Patent Application Laid-Open No. 61-172852), and so on have been proposed. However, the problem of the disadvantageous equilibrium cannot be solved merely by developing the catalyst, and hence there are very many issues to be solved including the reaction system in order to provide a process for the industrial production aiming for mass production.

Attempts have also been made to devise a reaction system so as to shift the equilibrium toward the product system as much as possible, and thus improve the yield of the aromatic carbonates. For example, for the reaction between dimethyl carbonate and phenol, there have been proposed a method in which by-produced methanol is distilled off by azeotropy together with an azeotrope-forming agent (see Patent Document 10: Japanese Patent Application Laid-Open No. 54-48732 (corresponding to West German Patent Application No; 736063, and U.S. Pat. No. 4,252,737)), and a method in which the methanol produced as the by-product is removed by being adsorbed onto a molecular sieve (see Patent Document 11: Japanese Patent Application Laid-Open No. 58-185536 (corresponding to U.S. Pat. No. 410,464)). Moreover, a method has also been proposed in which, using an apparatus in which a distillation column is provided on top of a reactor, an alcohol produced as the by-product in the reaction is separated off from the reaction mixture, and at the same time unreacted starting material that evaporates is separated off by distillation (see Patent Documents 12: examples in Japanese Patent Application Laid-Open No. 56-123948 (corresponding to U.S. Pat. No. 4,182,726), examples in Japanese Patent Application Laid-Open No. 56-25138, examples in Japanese Patent Application Laid-Open No. 60-169444 (corresponding to U.S. Pat. No. 4,554,110), examples in Japanese Patent Application Laid-Open No. 60-169445 (corresponding to U.S. Pat. No. 4,552,704), examples in Japanese Patent Application Laid-Open No. 60-173016 (corresponding to U.S. Pat. No. 4,609,501), examples in Japanese Patent Application Laid-Open No. 61-172852, examples in Japanese Patent Application Laid-Open No. 61-291545, examples in Japanese Patent Application Laid-Open No. 62-277345).

However, these reaction systems are basically batch system or switchover system. Because there is the limitation in the improvement of the reaction rate through catalyst development for such a transesterification reaction, and the reaction rate is still slow, and thus it has been thought that a batch system is preferable to a continuous system. Of these, a continuous stirring tank reactor (CSTR) system in which a distillation column is provided on top of a reactor has been proposed as a continuous system, but there are problems such as the reaction rate being slow, and a gas-liquid interface in the reactor being small, based on the volume of the liquid. Hence it is not possible to make the conversion high. Accordingly, it is difficult to attain the object of producing the aromatic carbonate continuously in large amounts stably for a prolonged period of time by means of the above-mentioned methods, and many issues remain to be resolved before economical industrial implementation is possible.

The present inventors have developed reactive distillation methods in which such a transesterification reaction is carried out in a continuous multi-stage distillation column simultaneously with separation by distillation, and have been the first in the world to disclose that such a reactive distillation system is useful for such a transesterification reaction, for example a reactive distillation method in which a dialkyl carbonate and an aromatic hydroxy compound are continuously fed into a multi-stage distillation column, and the reaction is carried out continuously inside the column in which a catalyst is present, while continuously withdrawing a low boiling point component containing an alcohol produced as a by-product by distillation and continuously withdrawing a component containing a produced alkyl aryl carbonate from a lower portion of the column (see Patent Document 13: Japanese Patent Application Laid-Open No. 3-291257), a reactive distillation method in which an alkyl aryl carbonate is continuously fed into the multi-stage distillation column, and the reaction is carried out continuously inside the column in which a catalyst is present, while continuously withdrawing by distillation a low boiling point component containing a dialkyl carbonate produced as a by-product and continuously withdrawing a component containing a produced diaryl carbonate from a lower portion of the column (see Patent Document 14: Japanese Patent Application Laid-Open No. 4-9358), a reactive distillation method in which these reactions are carried out using two continuous multi-stage distillation columns, and hence a diaryl carbonate is produced continuously while efficiently recycling a dialkyl carbonate produced as a by-product (see Patent Document 15: Japanese Patent Application Laid-Open No. 4-211038), and a reactive distillation method in which a dialkyl carbonate and an aromatic hydroxy compound or the like are continuously fed into the multi-stage distillation column, and a liquid that flows down through the column is withdrawn from a side outlet provided at an intermediate stage and/or a lowermost stage of the distillation column, and is introduced into a reactor provided outside the distillation column so as to bring about reaction, and is then introduced back in through a circulating inlet provided at a stage above the stage where the outlet is provided, whereby reaction is carried out in both the reactor and the distillation column (see Patent Documents 16: Japanese Patent Application Laid-Open No. 4-224547, Japanese Patent Application Laid-Open No. 4-230242, Japanese Patent Application Laid-Open No. 4-235951).

These reactive distillation methods proposed by the present inventors are the first to enable aromatic carbonates to be produced continuously and efficiently, and many similar reactive distillation systems based on the above disclosures have been proposed thereafter (see Patent Documents 17 to 32: Patent Document 17: International Publication No. 00/18720 (corresponding to U.S. Pat. No. 5,362,901), Patent Document 18: Italian Patent No. 01255746, Patent Document 19: Japanese Patent Application Laid-Open No. 6-9506 (corresponding to European Patent No. 0560159, and U.S. Pat. No. 5,282,965), Patent Document 20: Japanese Patent Application Laid-Open No. 6-41022 (corresponding to European Patent No. 0572870, and U.S. Pat. No. 5,362,901), Patent Documents 21: Japanese Patent Application Laid-Open No. 6-157424 (corresponding to European Patent No. 0582931, and U.S. Pat. No. 5,334,742), Japanese Patent Application Laid-Open No. 6-184058 (corresponding to European Patent No. 0582930, and U.S. Pat. No. 5,344,954), Patent Document 22: Japanese Patent Application Laid-Open No. 7-304713, Patent Document 23: Japanese Patent Application Laid-Open No. 9-40616, Patent Document 24: Japanese Patent Application Laid-Open No. 9-59225, Patent Document 25: Japanese Patent Application Laid-Open No. 9-110805, Patent Document 26: Japanese Patent Application Laid-Open No. 9-165357, Patent Document 27: Japanese Patent Application Laid-Open No. 9-173819, Patent Documents 28: Japanese Patent Application Laid-Open No. 9-176094, Japanese Patent Application Laid-Open No. 2000-191596, Japanese Patent Application Laid-Open No. 2000-191597, Patent Document 29: Japanese Patent Application Laid-Open No. 9-194436 (corresponding to European Patent No. 0785184, and U.S. Pat. No. 5,705,673), Patent Document 30: International Publication No. 00/18720 (corresponding to U.S. Pat. No. 6,093, 842), Patent Documents 31: Japanese Patent Application Laid-Open No. 2001-64234, Japanese Patent Application Laid-Open No. 2001-64235, Patent Document 32: International Publication No. 02/40439 (corresponding to U.S. Pat. Nos. 6,596,894, 6,596,895, and 6,600,061)).

Among reactive distillation systems, the present applicants have further proposed, as a method that enables highly pure aromatic carbonates to be produced stably for a prolonged period of time without a large amount of a catalyst being required, a method in which high boiling point material containing a catalyst component is reacted with an active substance and then separated off, and the catalyst component is recycled (see Patent Documents 31: Japanese Patent Application Laid-Open No. 2001-64234, Japanese Patent Application Laid-Open No. 2001-64235), and a method carried out while keeping a weight ratio of a polyhydric aromatic hydroxy compound in the reaction system to a catalyst metal at not more than 2.0 (see Patent Document 32: International Publication No. 02/40439 (corresponding to U.S. Pat. Nos. 6,596,894, 6,596,895, and 6,600,061)). Furthermore, the present inventors have proposed a method in which 70 to 99% by weight of phenol produced as a by-product in a polymerization process is used as a starting material, and diphenyl carbonate can be produced by means of the reactive distillation method. This diphenyl carbonate can be used as the raw material for polymerization of aromatic polycarbonates (see Patent Document 33: International Publication No. 97/11049 (corresponding to European Patent No. 0855384, and U.S. Pat. No. 5,872,275)).

However, in all of these prior art documents in which the production of aromatic carbonates using the reactive distillation method is proposed, there is no disclosure whatsoever of a specific process or apparatus enabling mass production on an industrial scale (e.g. not less than 1 ton per hour), nor is there any description suggesting such a process or apparatus. For example, the descriptions regarding the heights ($H_1$ and $H_2$, respectively: cm), the diameters ($D_1$ and $D_2$, respectively: cm), the numbers of stages ($n_1$ and $n_2$, respectively) of the pair of reactive distillation columns and the feeding rates of the raw material ($Q_1$ and $Q_2$, respectively: kg/hr) disclosed for producing diphenyl carbonate (DPC) from dimethyl carbonate and phenol are as summarized in the following table.

TABLE 1

| $H_1$ | $D_1$ | $n_1$ | $Q_1$ | $H_2$ | $D_2$ | $n_2$ | $Q_2$ | PATENT DOCU-MENT |
|---|---|---|---|---|---|---|---|---|
| 600 | 25 | 20 | 66 | 600 | 25 | 20 | 23 | 15 |
| 350 | 2.8 | — | 0.2 | 305 | 5~10 | 15+ PACK-ING | 0.6 | 21 |
| 500 | 5 | 50 | 0.6 | 400 | 8 | 50 | 0.6 | 23 |
| 100 | 4 | — | 1.4 | 200 | 4 | — | 0.8 | 24 |
| 300 | 5 | 40 | 1.5 | — | 5 | 25 | 0.7 | 28 |
| 1200 | 20 | 40 | 86 | 600 | 25 | 20 | 31 | 33 |
|  |  |  |  |  |  |  |  | 34 |
| 600 | — | 20 | 66 | 600 | — | 20 | 22 | 35 |

See Patent Document 34: Japanese Patent Application Laid-Open No. 11-92429 (corresponding to European Patent No. 1016648, and U.S. Pat. No. 6,262,210 See Patent document 35: Japanese Patent Application Laid-Open No. 9-255772 (corresponding to European Patent No. 0892001, and U.S. Pat. No. 5,747,609)

In other words, a pair of the biggest continuous multi-stage distillation columns used when carrying out this reaction using the reactive distillation system are those disclosed by the present applicants in Patent Documents 33 and 34. As can be seen from Table 1, the maximum values of the various conditions for the continuous multi-stage distillation columns disclosed for the above reaction are $H_1$=1200 cm, $H_2$=600 cm, $D_1$=20 cm, $D_2$=25 cm, $n_1$=$n_2$=50 (Patent Document 23), $Q_1$=86 kg/hr, and $Q_2$=31 kg/hr, and the amount of diphenyl carbonate produced has not exceeded approximately 6.7 kg/hr, which is not an amount produced on an industrial scale.

DISCLOSURE OF THE INVENTION

It is an object of the present invention to provide a specific process that enables aromatic carbonates containing a diaryl carbonate as a main product to be produced with high selectivity and high productivity stably for a prolonged period of time on an industrial scale of not less than 1 ton per hour using two continuous multi-stage distillation columns from a dialkyl carbonate and an aromatic monohydroxy compound.

Since the present inventors disclosed a process for producing aromatic carbonates using a continuous multi-stage distillation column, various proposals regarding processes for the production of aromatic carbonates by means of a reactive distillation method have been made. However, these have all been on a small scale and short operating time laboratory level, and there have been no disclosures whatsoever on a specific process or apparatus enabling mass production on an industrial scale. In view of these circumstances, the present inventors carried out studies aimed at discovering a specific process enabling an aromatic carbonate containing a diaryl carbonate as a main product to be produced with high selectivity and high productivity stably for a prolonged period of time on an industrial scale of not less than 1 ton per hour. As a result, the present inventors have reached to the present invention.

That is, in the first aspect of the present invention, there is provided:

1. A process for the production of an aromatic carbonate containing a diaryl carbonate as a main product from a dialkyl carbonate and an aromatic monohydroxy compound as a starting material, which comprises the steps of:

(i) continuously feeding said starting material into a first continuous multi-stage distillation column in which a catalyst is present;

(ii) carrying out the reaction in said first column to produce an alcohol and an alkyl aryl carbonate;

(iii) continuously withdrawing a first column low boiling point reaction mixture containing a produced alcohol from an upper portion of said first column in a gaseous form while continuously withdrawing a first column high boiling point reaction mixture containing an alkyl aryl carbonate from a lower portion of said first column in a liquid form;

(IV) continuously feeding said first column high boiling point reaction mixture into a second continuous multi-stage distillation column in which a catalyst is present and which is connected to said first column while carrying out the reaction in said second column to produce a dialkyl carbonate and a diaryl carbonate;

(V) continuously withdrawing a second column low boiling point reaction mixture containing said produced dialkyl carbonate from an upper portion of said second column in a gaseous form while continuously withdrawing a second column high boiling point reaction mixture containing said produced diaryl carbonate from a lower portion of said second column in a liquid form; wherein (a) a molar ratio of the dialkyl carbonate to the aromatic monohydroxy compound in said starting material which is fed continuously into said first continuous multi-stage distillation column is in a range of from 0.1 to 10;

(b) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \tag{1}$$

(2) said inside diameter $D_1$ (cm) of the column satisfies the following formula (2), $$100 \leq D_1 \leq 2000 \tag{2}$$

(3) a ratio of said length $L_1$ (cm) to said inside diameter $D_1$ (cm) of the column satisfies the following formula (3), $$2 \leq L_1/D_1 \leq 40 \tag{3}$$

(4) said number of stages $n_1$ satisfies the following formula (4), $$20 \leq n_1 \leq 120 \tag{4}$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \tag{5}$$

and (6) a ratio of said inside diameter $D_1$ (cm) of the column to said inside diameter $d_{12}$ (cm) of the liquid outlet satisfies the following formula (6), $$3 \leq D_1/d_{12} \leq 20 \tag{6};$$

(c) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \tag{7},$$

(2) said inside diameter $D_2$ (cm) of the column satisfies the following formula (8), $$100 \leq D_2 \leq 2000 \tag{8},$$

(3) a ratio of the length $L_2$ (cm) to said inside diameter $D_2$ (cm) of the column satisfies the following formula (9), $$2 \leq L_2/D_2 \leq 40 \tag{9},$$

(4) said number of stages $n_2$ satisfies the following formula (10), $$10 \leq n_2 \leq 80 \tag{10},$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \tag{11},$$

and (6) a ratio of said inside diameter $D_2$ (cm) of the column to said inside diameter $d_{22}$ (cm) of the liquid outlet satisfies the following formula (12), $$5 \leq D_2/d_{22} \leq 30 \tag{12}.$$

2. The process according to item 1, wherein distillation is carried out simultaneously in said step (ii) and said step (iv), 3. The process according to item 1 or 2, wherein an amount of said diaryl carbonate produced is not less than 1 ton per hour.

In another aspect of the process according to the present invention, there is provided:

4. In a process for the production of an aromatic carbonate containing a diaryl carbonate as a main product in which the aromatic carbonate containing the diaryl carbonate as the main product are produced continuously by taking a mixture of a dialkyl carbonate and an aromatic monohydroxy compound as a starting material, continuously feeding the starting material into a first continuous multi-stage distillation column in which a catalyst is present, carrying out the reaction and the distillation simultaneously said the first column, continuously withdrawing a first column low boiling point reaction mixture containing a produced alcohol from an upper portion of said first column in a gaseous form, continuously withdrawing a first column high boiling point reaction mixture containing a produced alkyl aryl carbonate from a lower portion of said first column in a liquid form, continuously feeding the first column high boiling point reaction mixture into a second continuous multi-stage distillation column in which a catalyst is present, carrying out the reaction and the distillation simultaneously in said second column, continuously withdrawing a second column low boiling point reaction mixture containing a produced dialkyl carbonate from an upper portion of said second column in a gaseous form, continuously withdrawing a second column high boiling point reaction mixture containing a produced diaryl carbonate from a lower portion of said second column in a liquid form while continuously feeding the second column low boiling point reaction mixture containing the dialkyl carbonate into the first continuous multi-stage distillation column, the improvement in which:

(a) a molar ratio of the dialkyl carbonate to the aromatic monohydroxy compound in said starting material which is fed continuously into said first continuous multi-stage distillation column is in a range of from 0.1 to 10;

(b) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \tag{1},$$

(2) said inside diameter $D_1$ (cm) of the column satisfies the following formula (2), $$100 \leq D_1 \leq 2000 \tag{2},$$

(3) a ratio of said length $L_1$ (cm) to said inside diameter $D_1$ (cm) of the column satisfies the following formula (3), $$2 \leq L_1/D_1 \leq 40 \tag{3},$$

(4) said number of stages $n_1$ satisfies the following formula (4), $$20 \leq n_1 \leq 120 \tag{4},$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \tag{5},$$

and (6) a ratio of said inside diameter $D_1$ (cm) of the column to said inside diameter $d_{12}$ (cm) of the liquid outlet satisfies the following formula (6), $$3 \leq D_1/d_{12} \leq 20 \tag{6};$$

(c) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \qquad (7),$$

(2) said inside diameter $D_2$ (cm) of the column satisfies the following formula (8), $$100 \leq D_2 \leq 2000 \qquad (8),$$

(3) a ratio of the length $L_2$ (cm) to said inside diameter $D_2$ (cm) of the column satisfies the following formula (9), $$2 \leq L_2/D_2 \leq 40 \qquad (9),$$

(4) said number of stages $n_2$ satisfies the following formula (10), $$10 \leq n_2 \leq 80 \qquad (10),$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \qquad (11), \text{ and}$$

(6) a ratio of said inside diameter $D_2$ (cm) of the column to said inside diameter $d_{22}$ (cm) of the liquid outlet satisfies the following formula (12), $$5 \leq D_2/d_{22} \leq 30 \qquad (12),$$

5. The process according to item 4, wherein an amount produced of the diaryl carbonate is not less than 1 ton per hour,
6. The process according to any one of items 1 to 5, wherein $d_{11}$ and $d_{12}$ satisfy the following formula (13), and $d_{21}$ and $d_{22}$ satisfy the following formula (14)

$$1 \leq d_{12}/d_{11} \leq 5 \qquad (13)$$

$$1 \leq d_{21}/d_{22} \leq 6 \qquad (14),$$

7. The process according to any one of items 1 to 6, wherein $L_1$, $D_1$, $L_1/D_1$, $n_1$, $D_1/d_{11}$, and $D_1/d_{12}$ for said first continuous multi-stage distillation column satisfy the following formulae: $2000 \leq L_1 \leq 6000$, $150 \leq D_1 \leq 1000$, $3 \leq L_1/D_1 \leq 30$, $30 \leq n_1 \leq 100$, $8 \leq D_1/d_{11} \leq 25$, and $5 \leq D_1/d_{12} \leq 18$, respectively, and
$L_2$, $D_2$, $L_2/D_2$, $n_2$, $D_2/d_{21}$, and $D_2/d_{22}$ for said second continuous multi-stage distillation column satisfy the following formulae: $2000 \leq L_2 \leq 6000$, $150 \leq D_2 \leq 1000$, $3 \leq L_2/D_2 \leq 30$, $15 \leq n_2 \leq 60$, $2.5 \leq D_2/d_{21} \leq 12$, and $7 \leq D_2/d_{22} \leq 25$, respectively,
8. The process according to any one of items 1 to 7, wherein $L_1$, $D_1$, $L_1/D_1$, $n_1$, $D_1/d_{11}$, and $D_1/d_{12}$ for said first continuous multi-stage distillation column satisfy the following formulae: $2500 \leq L_1 \leq 5000$, $200 \leq D_1 \leq 800$, $5 \leq L_1/D_1 \leq 15$, $40 \leq n_1 \leq 90$, $10 \leq D_1/d_{11} \leq 25$, and $7 \leq D_1/d_{12} \leq 15$, respectively, and
$L_2$, $D_2$, $L_2/D_2$, $n_2$, $D_2/d_{21}$, and $D_2/d_{22}$ for said second continuous multi-stage distillation column satisfy the following formulae: $2500 \leq L_2 \leq 5000$, $200 \leq D_2 \leq 800$, $5 \leq L_2/D_2 \leq 15$, $20 \leq n_2 \leq 50$, $3 \leq D_2/d_{21} \leq 10$, and $9 \leq D_2/d_{22} \leq 20$, respectively,
9. The process according to any one of items 1 to 8, wherein each of said first continuous multi-stage distillation column and said second continuous multi-stage distillation column is a distillation column having a tray and/or a packing as the internal,
10. The process according to item 9, wherein said first continuous multi-stage distillation column is a plate-type distillation column having the tray as the internal, and said second continuous multi-stage distillation column is a distillation column having both the packing and the tray as the internal,
11. The process according to item 9 or 10, wherein each of the trays in said first continuous multi-stage distillation column and said second continuous multi-stage distillation column is a sieve tray having a sieve portion and a down corner portion,
12. The process according to item 11, wherein said sieve tray has 100 to 1000 holes/m² in the sieve portion,
13. The process according to item 11 or 12, wherein the cross-sectional area per hole of said sieve tray is in a range of from 0.5 to 5 cm²,
14. The process according to item 9 or 10, wherein said second continuous multi-stage distillation column is a distillation column having, as said internal, the packing in an upper portion of the column, and the tray in a lower portion of the column,
15. The process according to any one of items 9 to 14, wherein said packing of said internal in said second continuous multi-stage distillation column is one or more of a structured packing,
16. The process according to item 15, wherein said structured packing in said second continuous multi-stage distillation column is of at least one selected from the group consisting of Mellapak, Gempak, TECHNO-PAK, FLEXI-PAK, a Sulzer packing, a Goodroll packing and a Glitchgrid,
17. The process according to any one of items 1 to 16, wherein said first continuous multi-stage distillation column comprises two or more of distillation columns,
18. The process according to any one of items 1 to 17, wherein said second continuous multi-stage distillation column comprises two or more of distillation columns.

In the second aspect of the present invention, there is provided:

19. An aromatic carbonate comprising a halogen content of not more than 0.1 ppm, produced by the process according to any one of items 1 to 18.

In the third aspect of the present invention, there is provided:

20. A reactive distillation apparatus comprising a first continuous multi-stage distillation column for carrying out reaction and distillation; and a second continuous multi-stage distillation column for carrying out reaction and distillation, which is connected to said first continuous multi-stage distillation column, comprising:

(a) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \qquad (1),$$

(2) said inside diameter $D_1$ (cm) of the column satisfies the following formula (2), $$100 \leq D_1 \leq 2000 \qquad (2),$$

(3) a ratio of said length $L_1$ (cm) to said inside diameter $D_1$ (cm) of the column satisfies the following formula (3), $$2 \leq L_1/D_1 \leq 40 \quad (3),$$

(4) said number of stages $n_1$ satisfies the following formula (4), $$20 \leq n_1 \leq 120 \quad (4),$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \quad (5), \text{ and}$$

(6) a ratio of said inside diameter $D_1$ (cm) of the column to said inside diameter $d_{12}$ (cm) of the liquid outlet satisfies the following formula (6), $$3 \leq D_1/d_{12} \leq 20 \quad (6);$$

(b) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \quad (7),$$

(2) said inside diameter $D_2$ (cm) of the column satisfies the following formula (8), $$100 \leq D_2 \leq 2000 \quad (8),$$

(3) a ratio of the length $L_2$ (cm) to said inside diameter $D_2$ (cm) of the column satisfies the following formula (9), $$2 \leq L_2/D_2 \leq 40 \quad (9)$$

(4) said number of stages $n_2$ satisfies the following formula (10), $$10 \leq n_2 \leq 80 \quad (10),$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \quad (11), \text{ and}$$

(6) a ratio of said inside diameter $D_2$ (cm) of the column to said inside diameter $d_{22}$ (cm) of the liquid outlet satisfies the following formula (12), $$5 \leq D_2/d_{22} \leq 30 \quad (12),$$

21. The reactive distillation apparatus according to item 20, wherein $d_{11}$ and $d_{12}$ satisfy the following formula (13), and $d_{21}$ and $d_{22}$ satisfy the following formula (14)

$$1 \leq d_{12}/d_{11} \leq 5 \quad (13)$$

$$1 \leq d_{21}/d_{22} \leq 6 \quad (14),$$

22. The reactive distillation apparatus according to item 20 or 21, wherein $L_1$, $D_1$, $L_1/D_1$, $n_1$, $D_1/d_{11}$, and $D_1/d_{12}$ for said first continuous multi-stage distillation column satisfy the following formulae: $2000 \leq L_1 \leq 6000$, $150 \leq D_1 \leq 1000$, $3 \leq L_1/D_1 \leq 30$, $30 \leq n_1 \leq 100$, $8 \leq D_1/d_{11} \leq 25$, and $5 \leq D_1/d_{12} \leq 18$, respectively, and $L_2$, $D_2$, $L_2/D_2$, $n_2$, $D_2/d_{21}$, and $D_2/d_{22}$ for said second continuous multi-stage distillation column satisfy the following formulae: $2000 \leq L_2 \leq 6000$, $150 \leq D_2 \leq 1000$, $3 \leq L_2/D_2 \leq 30$, $15 \leq n_2 \leq 60$, $2.5 \leq D_2/d_{21} \leq 12$, and $7 \leq D_2/d_{22} \leq 25$, respectively, 23. The reactive distillation apparatus according to any one of items 20 to 22, wherein $L_1$, $D_1$, $L_1/D_1$, $n_1$, $D_1/d_{11}$, and $D_1/d_{12}$ for said first continuous multi-stage distillation column satisfy the following formulae: $2500 \leq L_1 \leq 5000$, $200 \leq D_1 \leq 800$, $5 \leq L_1/D_1 \leq 15$, $40 \leq n_1 \leq 90$, $10 \leq D_1/d_{11} \leq 25$, and $7 \leq D_1/d_{12} \leq 15$, respectively, and $L_2$, $D_2$, $L_2/D_2$, $n_2$, $D_2/d_{21}$, and $D_2/d_{22}$ for said second continuous multi-stage distillation column satisfy the following formulae: $2500 \leq L_2 \leq 5000$, $200 \leq D_2 \leq 800$, $5 \leq L_2/D_2 \leq 15$, $20 \leq n_2 \leq 50$, $3 \leq D_2/d_{21} \leq 10$, and $9 \leq D_2/d_{22} \leq 20$, respectively, 24. The reactive distillation apparatus according to any one of items 20 to 23, wherein each of said first continuous multi-stage distillation column and said second continuous multi-stage distillation column is a distillation column having a tray and/or a packing as the internal, 25. The reactive distillation apparatus according to item 24, wherein said first continuous multi-stage distillation column is a plate-type distillation column having the tray as the internal, and said second continuous multi-stage distillation column is a distillation column having both the packing and the tray as the internal, 26. The reactive distillation apparatus according to item 24 or 25, wherein each of the trays in said first continuous multi-stage distillation column and said second continuous multi-stage distillation column is a sieve tray having a sieve portion and a down corner portion, 27. The reactive distillation apparatus according to item 26, wherein said sieve tray has 100 to 1000 holes/m$^2$ in the sieve portion, 28. The reactive distillation apparatus according to item 26 or 27, wherein the cross-sectional area per hole of said sieve tray is in a range of from 0.5 to 5 cm$^2$, 29. The process according to item 24 or 25, wherein said second continuous multi-stage distillation column is a distillation column having, as said internal, the packing in an upper portion of the column, and the tray in a lower portion of the column, 30. The reactive distillation apparatus according to any one of items 24 to 29, wherein said packing of said internal in said second continuous multi-stage distillation column is one or more of a structured packing, 31. The reactive distillation apparatus according to item 30, wherein said structured packing in said second continuous multi-stage distillation column is of at least one selected from the group consisting of Mellapak, Gempak, TECHNO-PAK, FLEXI-PAK, a Sulzer packing, a Goodroll packing and a Glitchgrid, 32. The reactive distillation apparatus according to any one of items 20 to 31, wherein said first continuous multi-stage distillation column comprises two or more of distillation columns, 33. The reactive distillation apparatus according to any one of items 20 to 32, wherein said second continuous multi-stage distillation column comprises two or more of distillation columns.

ADVANTAGEOUS EFFECTS OF THE INVENTION

It has been discovered that according to the present invention, from a dialkyl carbonate and an aromatic monohydroxy compound, an aromatic carbonate containing a diaryl carbonate as a main product can be produced on an industrial scale of not less than 1 ton per hour, preferably not less than 2 tons per hour, more preferably not less than 3 tons per hour, with a high selectivity of not less than 95%, preferably not less than 97%, more preferably not less than 99%, stably for a prolonged period of time of not less than 2000 hours, preferably not less than 3000 hours, more preferably not less than 5000 hours. A diaryl carbonate obtained by subjecting the aromatic carbonates containing the diaryl carbonate as a main component obtained through the present invention to separation/purification through distillation or the like is of high purity, and is useful as a raw material of a transesterification method polycarbonate or polyester carbonate or the like, or as a raw material of a non-phosgene method isocyanate or urethane or the like. Moreover, according to the present invention, because a starting material and catalyst not containing a halogen are generally used, the diaryl carbonate obtained has a halogen content of not more than 0.1 ppm, preferably not more than 10 ppb, more preferably not more than 1 ppb.

DESCRIPTION OF REFERENCE NUMERALS

Figure 1:
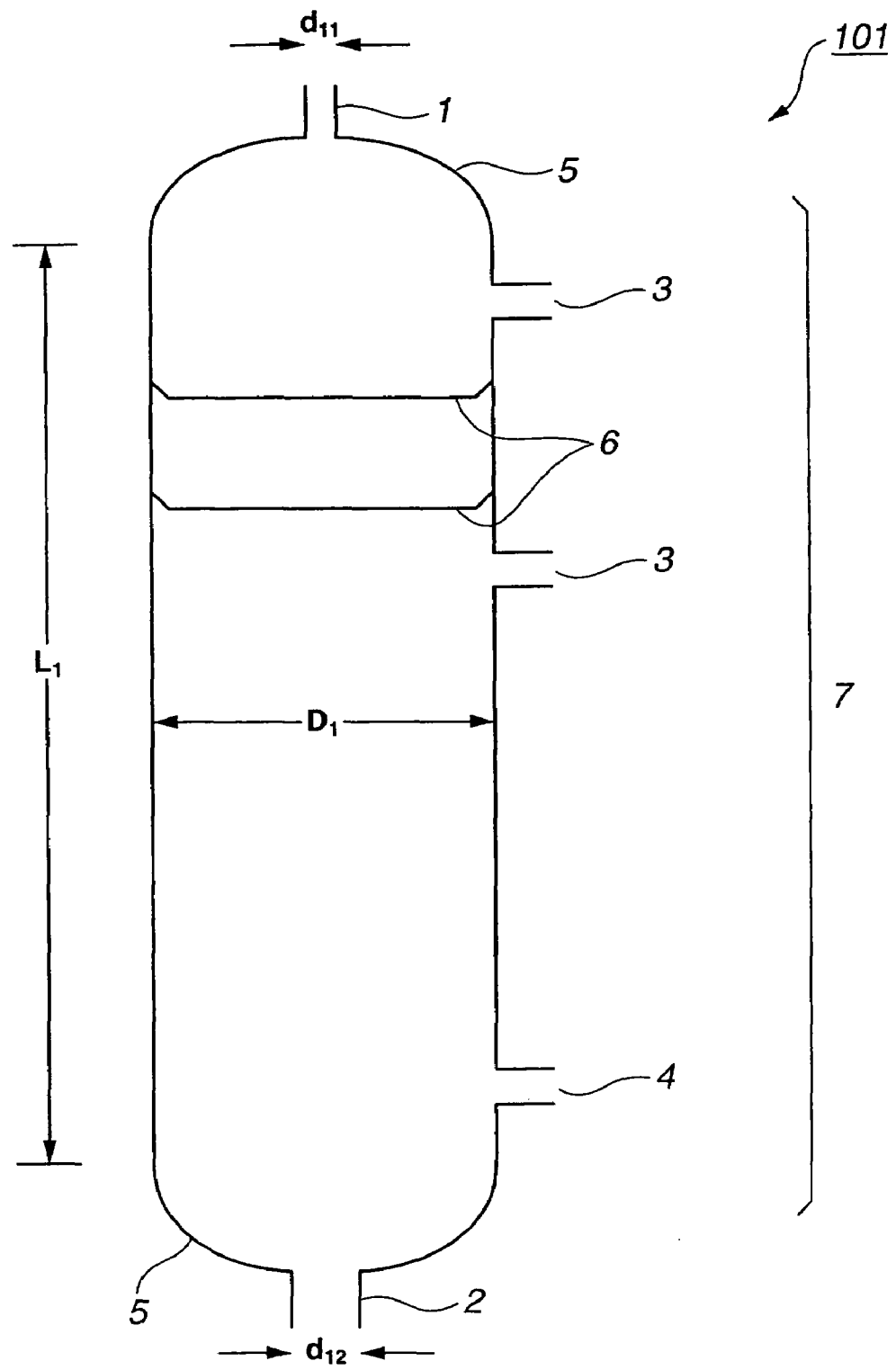
FIG. 1 is a schematic view of a first continuous multi-stage distillation column for carrying out the present invention, the distillation column having an internal provided inside a trunk portion thereof.

1: gas outlet, 2: liquid outlet, 3, 4, 15, 19, 25, 29: inlet, 5: end plate, 6: internal, 6-1: internal (packing), 6-2: internal (tray), 7: trunk portion, $L_1$, $L_2$: length of trunk portion (cm), $D_1$, $D_2$: inside diameter of trunk portion (cm), $d_{11}$, $d_{21}$: inside diameter of gas outlet (cm), $d_{12}$, $d_{22}$: inside diameter of liquid outlet (cm), 101: the first multi-stage distillation column, 201: the second multi-stage distillation column, 11, 12, 21: inlet, 13, 23; a column top gas outlet, 14, 24, 18, 28: heat exchanger, 15, 25: reflux liquid inlet, 16, 26: a column top component outlet, 17, 27: a column bottom liquid outlet, 31: a column bottom component outlet of the second multi-stage distillation column.

BEST MODE FOR CARRYING OUT THE INVENTION

In the following, the present invention is described in detail.

A dialkyl carbonate used in the present invention is a compound represented by the following formula (15).

(15)

wherein $R^1$ represents an alkyl group having 1 to 10 carbon atoms, an alicyclic group having 3 to 10 carbon atoms, or an aralkyl group having 6 to 10 carbon atoms. Examples of $R^1$ include alkyl groups such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; alicyclic groups such as cyclopropyl, cyclobutyl, cyclopentyl, cyclohexyl and cycloheptyl; and aralkyl groups such as benzyl, phenethyl (isomers), phenylpropyl (isomers), phenylbutyl (isomers) and methylbenzyl (isomers). The above-mentioned alkyl groups, alicyclic groups and aralkyl groups may be substituted with other substitutents such as a lower alkyl group, a lower alkoxy group, a cyano group or a halogen atom, and may also contain an unsaturated bond.

Examples of dialkyl carbonates having such $R^1$ include dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenethyl carbonate (isomers), di(phenylpropyl) carbonate (isomers), di(phenylbutyl)carbonate (isomers), di(chlorobenzyl)carbonate (isomers), di(methoxybenzyl) carbonate (isomers), di(methoxymethyl)carbonate, di(methoxyethyl)carbonate (isomers), di(chloroethyl)carbonate (isomers) and di(cyanoethyl)carbonate (isomers).

Of these dialkyl carbonates, ones preferably used in the present invention are dialkyl carbonates in which $R^1$ is an alkyl group having not more than four carbon atoms and not containing a halogen atom. A particularly preferable one is dimethyl carbonate. Moreover, of preferable dialkyl carbonates, particularly preferable ones are dialkyl carbonates produced in a state substantially not containing a halogen atom, for example, ones produced from an alkylene carbonate substantially not containing a halogen atom and an alcohol substantially not containing a halogen atom.

An aromatic monohydroxy compound used in the present invention is a compound represented by the following formula (16). The type of the aromatic monohydroxy compound is not limited, so long as the hydroxyl group is directly bonded to the aromatic group;

(16)

wherein $Ar^1$ represents an aromatic group having 5 to 30 carbon atoms. Examples of aromatic monohydroxy compounds having such $Ar^1$ include phenol; various alkylphenols such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols such as methoxyphenol (isomers) and ethoxyphenol (isomers); arylalkylphenols such as phenylpropylphenol (isomers); naphthol (isomers) and various substituted naphthols; and heteroaromatic monohydroxy compounds such as hydroxypyridine (isomers), hydroxycoumarin (isomers) and hydroxyquinoline (isomers).

Of these aromatic monohydroxy compounds, ones preferably used in the present invention are aromatic monohydroxy compounds in which $Ar^1$ is an aromatic group having 6 to 10 carbon atoms. Phenol is particularly preferable. Moreover, of these aromatic monohydroxy compounds, ones substantially not containing a halogen are preferably used in the present invention.

The molar ratio of the dialkyl carbonate to the aromatic monohydroxy compound used as the starting material of the present invention must be in a range of from 0.1 to 10. Outside this range, an amount of unreacted material remaining, based on a prescribed amount of the alkyl aryl carbonate produced becomes high, which is not efficient for the production of the aromatic carbonate. Moreover, much energy is required to recover the alkyl aryl carbonate. For such reasons, the above molar ratio is preferably in a range of from 0.5 to 5.0, more preferably 0.8 to 3.0, yet more preferably from 1.0 to 2.0.

In the present invention, not less than 1 ton per hour of the diaryl carbonate is produced continuously. The minimum amount of the aromatic monohydroxy compound fed in continuously for the above production is generally 15 P ton/hr, preferably 13 P ton/hr, more preferably 10 P ton/hr, based on the amount of the aromatic carbonate (P ton/hr) to be produced. More preferably, this amount can be made to be less than 8.0 P ton/hr.

The dialkyl carbonate and the aromatic monohydroxy compound used as the starting material of the present invention may be of high purity, or may contain other compounds, for example may contain compounds or reaction by-products produced in the first continuous multi-stage distillation column and/or the second continuous multi-stage distillation column. In the case of industrial implementation, for the starting material, besides fresh dialkyl carbonate and aromatic monohydroxy compound newly introduced into the reaction system, it is also preferable to use the dialkyl carbonate and the aromatic monohydroxy compound recovered from the first continuous multi-stage distillation column and/or the second continuous multi-stage distillation column. In the process of the present invention, the column top component that contains a low boiling point reaction mixture in the second continuous multi-stage distillation column are fed into the first continuous multi-stage distillation column. In this case, the second column low boiling point reaction mixture may be fed into the first continuous multi-stage distillation column as is, or after some of the components thereof have been separated out. Accordingly, in the present invention, which is implemented industrially, it is preferable for the starting material fed into the first continuous multi-stage distillation column to contain an alcohol, an alkyl aryl carbonate, a diaryl carbonate, an alkyl aryl ether, and so on. A starting material further containing small amounts of high boiling point by-products such as Fries rearrangement products of the alkyl aryl carbonate and diaryl carbonate which are the products, derivatives thereof, and so on can also be preferably used. In the present invention, for example, when producing methyl phenyl carbonate and diphenyl carbonate using as the starting material a mixture of dimethyl carbonate as the dialkyl carbonate and phenol as the aromatic monohydroxy compound, it is preferable for this starting material to contain methyl alcohol, and methyl phenyl carbonate and diphenyl carbonate, which are the reaction products, and the starting material may further contain small amounts of anisole, phenyl salicylate and methyl salicylate, which are reaction by-products, and high boiling point by-products derived therefrom.

The aromatic carbonates produced in the present invention refer to an alkyl aryl carbonate, a diaryl carbonate, or a mixture thereof, obtainable through the transesterification reaction between the dialkyl carbonate and the aromatic monohydroxy compound. Included under this transesterification reaction are a reaction in which one or two of the alkoxy groups of the dialkyl carbonate is/are exchanged with an aryloxy group of the aromatic monohydroxy compound so as to eliminate an alcohol, and a reaction in which two molecules of the alkyl aryl carbonate produced are converted into the diaryl carbonate and the dialkyl carbonate through a transesterification reaction therebetween, i.e. a disproportionation reaction. In the present invention, in the first continuous multi-stage distillation column, the alkyl aryl carbonate is mainly obtained, and in the second continuous multi-stage distillation column, the aromatic carbonates containing the diaryl carbonate as a main product are mainly obtainable through the disproportionation reaction of the alkyl aryl carbonate. In the present invention, it is particularly preferable for a starting material and catalyst not containing a halogen to be used; in this case, the diaryl carbonate produced does not contain a halogen at all, and hence it is important as a raw material when industrially producing a polycarbonate by means of the transesterification method. The reason for this is that if a halogen is present in the raw material for the polymerization even in a small amount of less than 1 ppm, then this may inhibit the polymerization reaction, or cause a deterioration of the properties of, or discoloration of, the polycarbonate produced.

As a catalyst used in the first continuous multi-stage distillation column and/or the second continuous multi-stage distillation column according to the present invention, for example, a metal-containing compound selected from the following compounds can be used:

<Lead Compounds>

Lead oxides such as $PbO$, $PbO_2$ and $Pb_3O_4$; lead sulfides such as $PbS$ and $Pb_2S$; lead hydroxides such as $Pb(OH)_2$ and $Pb_2O_2(OH)_2$; plumbites such as $Na_2PbO_2$, $K_2PbO_2$, $NaHPbO_2$ and $KHPbO_2$; plumbates such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof such as $PbCO_3$ and $2PbCO_3 \cdot Pb(OH)_2$; lead salts of organic acids, and carbonates and basic salts thereof, such as $Pb(OCOCH_3)_2$, $Pb(OCOCH_3)_4$ and $Pb(OCOCH_3)_2 \cdot PbO \cdot 3H_2O$, organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ (wherein Bu represents a butyl group, and Ph represents a phenyl group); alkoxylead compounds and aryloxylead compounds such as $Pb(OCH_3)_2$, $(CH_3O)Pb(OPh)$ and $Pb(OPh)_2$; lead alloys such as Pb—Na, Pb—Ca, Pb—Ba, Pb—Sn and Pb—Sb; lead minerals such as galena and zinc blende; and hydrates of such lead compounds;

<Copper Family Metal Compounds>

Salts and complexes of copper family metals such as $CuCl$, $CuCl_2$, $CuBr$, $CuBr_2$, $CuI$, $CuI_2$, $Cu(OAc)_2$, $Cu(acac)_2$, copper oleate, $Bu_2Cu$, $(CH_3O)_2Cu$, $AgNO_3$, $AgBr$, silver picrate, $AgC_6H_6ClO_4$, $[AuC{\equiv}C{-}C(CH_3)_3]_n$ and $[Cu(C_7H_8)Cl]_4$ (wherein acac represents an acetylacetone chelate ligand);

<Alkali Metal Complexes>

Alkali metal complexes such as $Li(acac)$ and $LiN(C_4H_9)_2$;

<Zinc Complexes>

Zinc complexes such as $Zn(acac)_2$;

<Cadmium Complexes>

Cadmium complexes such as $Cd(acac)_2$;

<Iron Family Metal Compounds>

Complexes of iron family metals such as $Fe(C_{10}H_8)(CO)_5$, $Fe(CO)_5$, $Fe(C_4H_6)(CO)_3$, $Co(mesitylene)_2$, $(PEt_2Ph)_2$, $CoC_5F_5(CO)_7$, $Ni\text{-}\pi\text{-}C_5H_5NO$ and ferrocene;

<Zirconium Complexes>

Zirconium complexes such as $Zr(acac)_4$ and zirconocene;

<Lewis Acid Type Compounds>

Lewis acids and Lewis acid-forming transition metal compounds such as $AlX_3$, $TiX_3$, $TiX_4$, $VOX_3$, $VX_5$, $ZnX_2$, $FeX_3$ and $SnX_4$ (wherein X represents a halogen atom, an acetoxy group, an alkoxy group or an aryloxy group); and <Organo-Tin Compounds>

Organo-tin compounds such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and $BuSnO(OH)$.

Each of these catalysts may be a solid catalyst fixed inside the multi-stage distillation column, or may be a soluble catalyst that dissolves in the reaction system.

Each of these catalyst components may of course have been reacted with an organic compound present in the reaction system such as an aliphatic alcohol, the aromatic monohydroxy compound, the alkyl aryl carbonate, the diaryl carbonate or the dialkyl carbonate, or may have been subjected to heating treatment with the starting material or products prior to the reaction.

In the case of carrying out the present invention with a soluble catalyst that dissolves in the reaction system, the catalyst is preferably one having a high solubility in the reaction liquid under the reaction conditions. Examples of preferable catalysts in this sense include $PbO$, $Pb(OH)_2$ and $Pb(OPh)_2$; $TiCl_4$, $Ti(OMe)_4$, $(MeO)Ti(OPh)_3$, $(MeO)_2Ti(OPh)_2$, $(MeO)_3Ti(OPh)$ and $Ti(OPh)_4$; $SnCl_4$, $Sn(OPh)_4$, $Bu_2SnO$ and $Bu_2Sn(OPh)_2$; $FeCl_3$, $Fe(OH)_3$ and $Fe(OPh)_3$; and such catalysts that have been treated with phenol, the reaction liquid or the like.

FIG. 1 shows a schematic view of the first continuous multi-stage distillation column for carrying out a production process according to the present invention. The continuous multi-stage distillation column 101 used in the present invention comprises a structure having a pair of end plates 5 above and below a cylindrical trunk portion 7 having a length $L_1$ (cm) and an inside diameter $D_1$ (cm), and having an internal 6 with a number of stages n thereinside, and has a gas outlet 1 having an inside diameter $d_{11}$ (cm) at the top of the column or in an upper portion of the column near to the top, a liquid outlet 2 having an inside diameter $d_{12}$ (cm) at the bottom of the column or in a lower portion of the column near to the bottom, at least one inlet 3 provided in the upper portion and/or a middle portion of the column below the gas outlet, and at least one inlet 4 provided in the lower portion of the column above the liquid outlet.

More specifically, the following are required for the first continuous multi-stage distillation column 101 according to the present invention:

(1) the length $L_1$ (cm) must satisfy formula (1), $$1500 \leq L_1 \leq 8000 \qquad (1),$$

(2) the inside diameter D1 (cm) of the column must satisfy formula (2), $$100 \leq D_1 \leq 2000 \qquad (2),$$

(3) a ratio of the length $L_1$ (cm) to the inside diameter $D_1$ (cm) of the column must satisfy formula (3), $$2 \leq L_1/D_1 \leq 40 \qquad (3),$$

(4) the number of stages $n_1$ must satisfy formula (4), $$20 \leq n_1 \leq 120 \qquad (4),$$

(5) a ratio of the inside diameter $D_1$ (cm) of the column to the inside diameter $d_{11}$ (cm) of the gas outlet must satisfy formula (5), $$5 \leq D_1/d_{11} \leq 30 \qquad (5), \text{ and}$$

(6) a ratio of the inside diameter $D_1$ (cm) of the column to the inside diameter $d_{12}$ (cm) of the liquid outlet must satisfy formula (6), $$3 \leq D_1/d_{12} \leq 20 \qquad (6).$$

Figure 2:
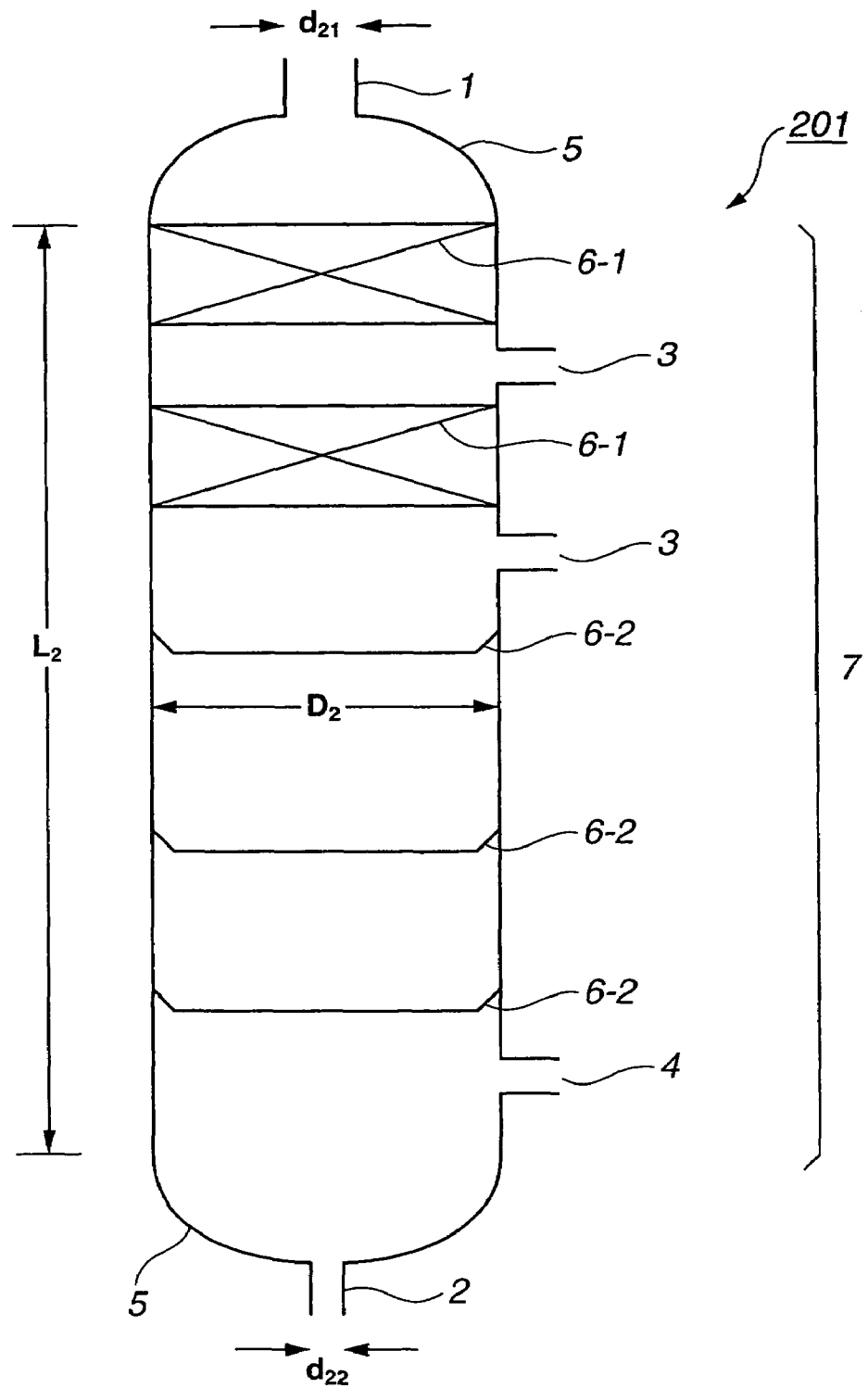
FIG. 2 is a schematic view of a second continuous multi-stage distillation column preferable for carrying out the present invention, the distillation column having, provided inside a trunk portion thereof, an internal comprising a structured packing (6-1) in an upper portion and a sieve tray (6-2) in a lower portion.

FIG. 2 shows a schematic view of the second continuous multi-stage distillation column for carrying out a production process according to the present invention. The second continuous multi-stage distillation column 201 used in the present invention comprises a structure having a pair of end plates 5 above and below a cylindrical trunk portion 7 having a length $L_2$ (cm) and an inside diameter $D_2$ (cm), and having an internal (6-1: packing, 6-2: tray) with a number of stages $n_2$ thereinside, and has a gas outlet 1 having an inside diameter $d_{21}$ (cm) at the top of the column or in an upper portion of the column near to the top, a liquid outlet 2 having an inside diameter $d_{22}$ (cm) at the bottom of the column or in a lower portion of the column near to the bottom, at least one inlet 3 provided in the upper portion and/or a middle portion of the column below the gas outlet, and at least one inlet 4 provided in the lower portion of the column above the liquid outlet.

More specifically, the following are required for the second continuous multi-stage distillation column 201 according to the present invention:

(1) the length $L_2$ (cm) must satisfy formula (7), $$1500 \leq L_2 \leq 8000 \qquad (7),$$

(2) the inside diameter $D_2$ (cm) of the column must satisfy formula (8), $$100 \leq D_2 \leq 2000 \qquad (8),$$

(3) a ratio of the length $L_2$ (cm) to the inside diameter $D_2$ (cm) of the column must satisfy formula (9), $$2 \leq L_2/D_2 \leq 40 \qquad (9),$$

(4) the number of stages $n_2$ must satisfy formula (10), $$10 \leq n_2 \leq 80 \qquad (10),$$

(5) a ratio of the inside diameter $D_2$ (cm) of the column to the inside diameter $d_{21}$ (cm) of the gas outlet must satisfy formula (11), $$2 \leq D_2/d_{21} \leq 15 \qquad (11), \text{ and}$$

(6) a ratio of the inside diameter $D_2$ (cm) of the column to the inside diameter $d_{22}$ (cm) of the liquid outlet must satisfy formula (12), $$5 \leq D_2/d_{22} \leq 30 \qquad (12).$$

Note that since FIGS. 1 and 2 show embodiments of the continuous multi-stage distillation columns according to the present invention, arrangement of the internal is not limited to that of FIGS. 1 and 2. It should be noted that the term "in an upper portion of the column near to the top" refers to the portion extending downwardly from the top of the column to the location measuring about 0.25 $L_1$ or 0.25 $L_2$, and the term "in a lower portion of the column near to the bottom" refers to the portion extending upwardly from the bottom of the column to the location measuring about $0.25L_1$ or $0.25L_2$. Note that $L_1$ and L2 are defined above.

It has been discovered that by using the first continuous multi-stage distillation column and the second continuous multi-stage distillation column that simultaneously satisfy formulae (1) to (12), aromatic carbonates containing a diaryl carbonate as a main product can be produced from a dialkyl carbonate and an aromatic monohydroxy compound on an industrial scale of not less than 1 ton per hour with high selectivity and high productivity stably for a prolonged period of time, for example not less than 2000 hours, preferably not less than 3000 hours, more preferably not less than 5000 hours. The reason why it has become possible to produce aromatic carbonates on an industrial scale with such excellent effects by implementing the process of the present invention is not clear, but this is supposed to be due to a combined effect brought about when the conditions of formulae (1) to (12) are combined. Preferable ranges for the respective factors are described below.

If each of $L_1$ (cm) and $L_2$ (cm) is less than 1500, then the conversion decreases and hence it is not possible to attain the desired production amount. Moreover, to keep down the equipment cost while securing the conversion enabling the desired production amount to be attained, each of $L_1$ and $L_2$ must be made to be not more than 8000. More preferable ranges for $L_1$ (cm) and $L_2$ (cm) are $2000 \leq L_1 \leq 6000$ and $2000 \leq L_2 \leq 6000$, respectively with $2500 \leq L_1 \leq 5000$ and $2500 \leq L_2 \leq 5000$ being yet more preferable.

If each of $D_1$ (cm) and $D_2$ (cm) is less than 100, then it is not possible to attain the desired production amount. Moreover, to keep down the equipment cost while attaining the desired production amount, each of $D_1$ and $D_2$ must be made to be not more than 2000. More preferable ranges for $D_1$ (cm) and $D_2$ (cm) are $150 \leq D_1 \leq 1000$ and $150 \leq D_2 \leq 1000$, respectively with $200 \leq D_1 \leq 800$ and $200 \leq D_2 \leq 800$ being yet more preferable. For the first continuous multi-stage distillation column and the second continuous multi-stage distillation column, so long as $D_1$ and $D_2$ are within the above ranges, each of the columns may have the same inside diameter from the upper portion thereof to the lower portion thereof, or the inside diameter may differ from different portions. For example, for each of the continuous multi-stage distillation columns, the inside diameter of the upper portion of the column may be smaller than, or larger than, the inside diameter of the lower portion of the column.

If each of $L_1/D_1$ and $L_2/D_2$ is less than 2 or greater than 40, then stable operation becomes difficult. In particular, if $L_1/D_1$ or $L_2/D_2$ is greater than 40, then the pressure difference between the top and bottom of the column becomes too great, and hence prolonged stable operation becomes difficult. Moreover, it becomes necessary to increase the temperature in the lower portion of the column, and hence side reactions become liable to occur, bringing about a decrease in the selectivity. More preferable ranges for $L_1/D_1$ and $L_2/D_2$ are $3 \leq L_1/D_1 \leq 30$ and $3 \leq L_2/D_2 \leq 30$, respectively with $5 \leq L_1/D_1 \leq 15$ and $5 \leq L_2/D_2 \leq 15$ being yet more preferable.

If $n_1$ is less than 20, then the conversion decreases and it is not possible to attain the desired production amount for the first continuous multi-stage distillation column. Moreover, to keep down the equipment cost while securing the conversion enabling the desired production amount to be attained, $n_1$ must be made to be not more than 120. Furthermore, if $n_1$ is greater than 120, then the pressure difference between the top and bottom of the column becomes too great, and hence prolonged stable operation of the first continuous multi-stage distillation column becomes difficult. Moreover, it becomes necessary to increase the temperature in the lower portion of the column, and hence side reactions become liable to occur, bringing about a decrease in the selectivity. A more preferable range for $n_1$ is $30 \leq n_1 \leq 100$, with $40 \leq n_1 \leq 90$ being yet more preferable. Moreover, if $n_2$ is less than 10, then the conversion decreases and it is not possible to attain the desired production amount for the second continuous multi-stage distillation column. Moreover, to keep down the equipment cost while securing the conversion enabling the desired production amount to be attained, $n_2$ must be made to be not more than 80. Furthermore, if $n_2$ is greater than 80, then the pressure difference between the top and bottom of the column becomes too great, and hence prolonged stable operation of the second continuous multi-stage distillation column becomes difficult. Moreover, it becomes necessary to increase the temperature in the lower portion of the column, and hence side reactions become liable to occur, bringing about a decrease in the selectivity. A more preferable range for $n_2$ is $15 \leq n_2 \leq 60$, with $20 \leq n_2 \leq 50$ being yet more preferable.

If $D_1/d_{11}$ is less than 5, then the equipment cost for the first continuous multi-stage distillation column becomes high. Moreover, large amounts of gaseous components are readily released to the outside of the system, and hence stable operation of the first continuous multi-stage distillation column becomes difficult. If $D_1/d_{11}$ is greater than 30, then the gaseous component withdrawal amount becomes relatively low, and hence stable operation becomes difficult, and moreover a decrease in the conversion is brought about. A more preferable range for $D_1/d_{11}$ is $8 \leq D_1/d_{11} \leq 25$, with $10 \leq D_1/d_{11} \leq 20$ being yet more preferable. Furthermore, if $D_2/d_{21}$ is less than 2, then the equipment cost for the second continuous multi-stage distillation column becomes high. Moreover, large amounts of gaseous components are readily released to the outside of the system, and hence stable operation of the second continuous multi-stage distillation column becomes difficult. If $D_2/d_{21}$ is greater than 15, then the gaseous component withdrawal amount becomes relatively low, and hence stable operation becomes difficult, and moreover a decrease in the conversion is brought about. A more preferable range for $D_2/d_{21}$ is $5 \leq D_2/d_{21} \leq 12$, with $3 \leq D_2/d_{21} \leq 10$ being yet more preferable.

If $D_1/d_{12}$ is less than 3, then the equipment cost for the first continuous multi-stage distillation column becomes high. Moreover, the liquid withdrawal amount becomes relatively high, and hence stable operation of the first continuous multi-stage distillation column becomes difficult. If $D_1/d_{12}$ is greater than 20, then the flow rate through the liquid outlet and piping becomes excessively fast, and hence erosion becomes liable to occur, bringing about corrosion of the apparatus. A more preferable range for $D_1/d_{12}$ is $5 \leq D_1/d_{12} \leq 18$, with $7 \leq D_1/d_{12} \leq 15$ being yet more preferable. Furthermore, if $D_2/d_{22}$ is less than 5, then the equipment cost for the second continuous multi-stage distillation column becomes high. Moreover, the liquid withdrawal amount becomes relatively high, and hence stable operation of the second continuous multi-stage distillation column becomes difficult. If $D_2/d_{22}$ is greater than 30, then the flow rate through the liquid outlet and piping becomes excessively fast, and hence erosion becomes liable to occur, bringing about corrosion of the apparatus. A more preferable range for $D_2/d_{22}$ is $7 \leq D_2/d_{22} \leq 25$, with $9 \leq D_2/d_{22} \leq 20$ being yet more preferable.

Furthermore, it has been found that in the present invention it is further preferable for $d_{11}$ and $d_{12}$ to satisfy the formula (13), and for $d_{21}$ and $d_{22}$ to satisfy the formula (14).

$$1 \leq d_{12}/d_{11} \leq 5 \tag{13}$$

$$1 \leq d_{21}/d_{22} \leq 6 \tag{14}$$

The term "prolonged stable operation" used in the present invention means that operation can be carried out continuously in a steady state based on the operating conditions with no clogging of piping or erosion for not less than 1000 hours, preferably not less than 3000 hours, more preferably not less than 5000 hours, and a prescribed amount of the aromatic carbonates containing the diaryl carbonate as a main product can be produced while maintaining high selectivity.

A characteristic feature of the present invention is that the aromatic carbonates can be produced stably for a prolonged period of time with high selectivity and with a high productivity of not less than 1 ton per hour, preferably not less than 2 tons per hour, more preferably not less than 3 tons per hour. Moreover, another characteristic feature of the present invention is that in the case that $L_1$, $D_1$, $L_1/D_1$, $n_1$, $D_1/d_{11}$, and $D_1/d_{12}$ for the first continuous multi-stage distillation column satisfy the following formulae: $2000 \leq L_1 \leq 6000$, $150 \leq D_1 \leq 1000$, $3 \leq L_1/D_1 \leq 30$, $30 \leq n_1 \leq 100$, $8 \leq D_1/d_{11} \leq 25$, and $5 \leq D_1/d_{12} \leq 18$, respectively, and $L_2$, $D_2$, $L_2/D_2$, $n_2$, $D_2/d_{21}$ and $D_2/d_{22}$ for the second continuous multi-stage distillation column satisfy the following formulae: $2000 \leq L_2 \leq 6000$, $150 \leq D_2 \leq 1000$, $3 \leq L_2/D_2 \leq 30$, $15 \leq n_2 \leq 60$, $2.5 \leq D_2/d_{21} \leq 12$, and $7 \leq D_2/d_{22} \leq 25$, respectively, not less than 2 tons per hour, preferably not less than 2.5 tons per hour, more preferably not less than 3 tons per hour of the aromatic carbonates can be produced. Furthermore, another characteristic feature of the present invention is that in the case that $L_1$, $D_1$, $L_1/D_1$, $n_1$, $D_1/d_{11}$, and $D_1/d_{12}$ for the first continuous multi-stage distillation column satisfy the following formulae: $2500 \leq L_1 \leq 5000$, $200 \leq D_1 \leq 800$, $5 \leq L_1/D_1 \leq 15$, $40 \leq n_1 \leq 90$, $10 \leq D_1/d_{11} \leq 25$, and $7 \leq D_1/d_{12} \leq 15$, respectively and $L_2$, $D_2$, $L_2/D_2$, $n_2$, $D_2/d_{21}$, and $D_2/d_{22}$ for the second continuous multi-stage distillation column satisfy the following formulae: $2500 \leq L_2 \leq 5000$, $200 \leq D_2 \leq 800$, $5 \leq L_2/D_2 \leq 10$, $20 \leq n_2 \leq 50$, $3 \leq D_2/d_{21} \leq 10$, and $9 \leq D_2/d_{22} \leq 20$, respectively, not less than 3 tons per hour, preferably not less than 3.5 tons per hour, more preferably not less than 4 tons per hour of the aromatic carbonates can be produced.

"Selectivity for the aromatic carbonates" in the present invention is based on the aromatic monohydroxy compound reacted. In the present invention, a high selectivity of not less than 95% can generally be attained, preferably not less than 97%, more preferably not less than 98%.

Each of the first continuous multi-stage distillation column and the second continuous multi-stage distillation column used in the present invention is preferably a distillation column having a tray and/or a packing as the internal. The term "internal" used in the present invention means the parts in the distillation column where gas and liquid are actually brought into contact with one another. As the tray, for example, a bubble-cap tray, a sieve tray, a valve tray, a counterflow tray, a Superfrac tray, a Maxfrac tray, or the like are preferable. As the packing, a random packing such as a Raschig ring, a Lessing ring, a Pall ring, a Berl saddle, an Intalox saddle, a Dixon packing, a McMahon packing or a Heli-Pak, or a structured packing such as Mellapak, Gempak, TECHNO-PAK, FLEXI-PAK, a Sulzer packing, a Goodroll packing or a Glitchgrid are preferable. The multi-stage distillation column having both a tray portion and a portion packed with the packing can also be used. Note that the term "number of stages (n) of an internal" used in the present invention means that the total number of trays in the case of a tray, and the theoretical number of stages in the case of a packing. Therefore, in the case of the multi-stage column having both the tray portion and the portion packed with the packing, n means the sum of the total number of trays and the theoretical number of stages of the packing.

In the first continuous multi-stage distillation column of the present invention, a reaction in which the alkyl aryl carbonate is produced from the dialkyl carbonate and the aromatic monohydroxy compound mainly occurs. This reaction has an extremely low equilibrium constant, and the reaction rate is slow, and hence it has been discovered that a plate-type distillation column having the tray as the internal is particularly preferable as the first continuous multi-stage distillation column used in the reactive distillation. Moreover, in the second continuous multi-stage distillation column, it is mainly a disproportionation reaction of the alkyl aryl carbonate that occurs. This reaction also has a low equilibrium constant, and a slow reaction rate. It has been discovered that a distillation column having both the packing and the tray as the internal is preferable as the second continuous multi-stage distillation column used in the reactive distillation. Furthermore, it has been discovered that a distillation column having the packing installed in the upper portion thereof and the tray installed in the lower portion thereof is preferable as the second continuous multi-stage distillation column. It has been discovered that the packing in the second continuous multi-stage distillation column is preferably structured packing. Of the structured packing, Mellapak is particularly preferable.

Furthermore, it has been discovered that, as each of the tray installed in the first continuous multi-stage distillation column and the second continuous multi-stage distillation column, a sieve tray having a sieve portion and a down corner portion is particularly good in terms of the relationship between performance and equipment cost. It has also been discovered that the sieve tray preferably has 100 to 1000 holes/m$^2$ in the sieve portion. A more preferable number of holes is 120 to 900 holes/m$^2$, yet more preferably 150 to 800 holes/m$^2$. Moreover, it has been discovered that the cross-sectional area per hole of the sieve tray is preferably in a range of from 0.5 to 5 cm$^2$. A more preferable cross-sectional area per hole is 0.7 to 4 cm$^2$, yet more preferably 0.9 to 3 cm$^2$. Furthermore, it has been discovered that it is particularly preferable if the sieve tray has 100 to 1000 holes/m$^2$ in the sieve portion and the cross-sectional area per hole is in a range of from 0.5 to 5 cm$^2$. It has been shown that by adding the above conditions to the continuous multi-stage distillation columns, the object of the present invention can be attained more easily.

When carrying out the present invention, aromatic carbonates containing a diaryl carbonate as a main product are continuously produced by continuously feeding a dialkyl carbonate and an aromatic monohydroxy compound which are the starting material into the first continuous multi-stage distillation column in which a catalyst is present, carrying out the reaction and the distillation simultaneously in the first column, continuously withdrawing a first column low boiling point reaction mixture containing a produced alcohol from an upper portion of the first column in a gaseous form, continuously withdrawing a first column high boiling point reaction mixture containing a produced alkyl aryl carbonate from a lower portion of the first column in a liquid form, continuously feeding the first column high boiling point reaction mixture into the second continuous multi-stage distillation column in which a catalyst is present, carrying out the reaction and the distillation simultaneously in the second column, continuously withdrawing a second column low boiling point reaction mixture containing a produced dialkyl carbonate from an upper portion of the second column in a gaseous form, continuously withdrawing a second column high boiling point reaction mixture containing a produced diaryl carbonate from a lower portion of the second column in a liquid form while continuously feeding the second column low boiling point reaction mixture containing the dialkyl carbonate into the first continuous multi-stage distillation column.

As described above, the starting material may contain the alcohol, the alkyl aryl carbonate and the diaryl carbonate that are reaction products, and reaction by-products such as an alkyl aryl ether and high boiling point compounds. Taking into consideration the equipment and cost required for separation and purification in other processes, when actually implementing the present invention industrially, it is preferable for the starting material to contain small amounts of such compounds.

In the present invention, when continuously feeding the dialkyl carbonate and the aromatic monohydroxy compound which are the starting material into the first continuous multi-stage distillation column, this starting material may be fed into the first distillation column in a liquid form and/or a gaseous form from inlet(s) provided in one or more of positions in the upper portion or the middle portion of the first distillation column below the gas outlet in the upper portion of the first distillation column. It is also preferable to feed a starting material containing a large proportion of the aromatic monohydroxy compound into the first distillation column in a liquid form from an inlet provided in the upper portion of the first distillation column, and feed a starting material containing a large proportion of the dialkyl carbonate into the first distillation column in a gaseous form from an inlet provided in the lower portion of the first distillation column above the liquid outlet in the lower portion of the first distillation column.

Moreover, in the present invention, the first column high boiling point reaction mixture containing the alkyl aryl carbonate continuously withdrawn from the lower portion of the first continuous multi-stage distillation column is continuously fed into the second continuous multi-stage distillation column. Here, the first column high boiling point reaction mixture is preferably fed into the second distillation column in a liquid form and/or a gaseous form from inlet(s) provided in one or more of positions in the upper portion or the middle portion of the second distillation column below the gas outlet in the upper portion of the second distillation column. Moreover, in the case of using, as the second distillation column, a distillation column having a packing portion in the upper portion thereof and a tray portion in the lower portion thereof, which is a preferable embodiment of the present invention, it is preferable for at least one position where an inlet is installed to be between the packing portion and the tray portion. Moreover, in the case that the packing comprise a plurality of structured packings, it is preferable for an inlet to be installed in a space between the structured packings.

Moreover, in the present invention, it is also preferable to carry out a reflux operation of condensing the gaseous component withdrawn from the top of each of the first continuous multi-stage distillation column and the second continuous multi-stage distillation column, and then returning some of this component into the upper portion of that distillation column. In this case, the reflux ratio for the first continuous multi-stage distillation column is in a range of from 0 to 10, and the reflux ratio for the second continuous multi-stage distillation column is in a range of from 0.01 to 10, preferably 0.08 to 5, more preferably 0.1 to 2. For the first continuous multi-stage distillation column, not carrying out such a reflux operation (i.e. reflux ratio=0) is also a preferable embodiment.

In the present invention, the method of making the catalyst be present in the first continuous multi-stage distillation column may be any method. In the case that the catalyst is a solid that is insoluble in the reaction liquid, it is preferable for the catalyst to be fixed inside the column by, for example, being installed on a plate inside the first continuous multi-stage distillation column or being installed in the form of a packing. In the case of a catalyst that dissolves in the starting material or the reaction liquid, it is preferable to feed the catalyst into the first distillation column from a position above the middle portion of the first distillation column. In this case, the catalyst liquid dissolved in the starting material or reaction liquid may be introduced into the column together with the starting material, or may be introduced into the column from a different inlet to the starting material. The amount of the catalyst used in the first continuous multi-stage distillation column in the present invention varies depending on the type of catalyst used, the types and proportions of the starting material compounds, and reaction conditions such as the reaction temperature and the reaction pressure. The amount of the catalyst is generally in a range of from 0.0001 to 30% by weight, preferably 0.005 to 10% by weight, more preferably 0.001 to 1% by weight, based on the total weight of the starting material.

Moreover, in the present invention, the method of making the catalyst be present in the second continuous multi-stage distillation column may be any method. In the case that the catalyst is a solid that is insoluble in the reaction liquid, it is preferable for the catalyst to be fixed inside the column by, for example, being installed on a plate inside the second continuous multi-stage distillation column or being installed in the form of a packing. In the case of a catalyst that dissolves in the starting material or the reaction liquid, it is preferable to feed the catalyst into the second distillation column from a position above the middle portion of the second distillation column. In this case, the catalyst liquid dissolved in the starting material or reaction liquid may be introduced into the column together with the starting material, or may be introduced into the column from a different inlet to the starting material. The amount of the catalyst used in the second continuous multi-stage distillation column in the present invention varies depending on the type of catalyst used, the types and proportions of the starting material compounds, and reaction conditions such as the reaction temperature and the reaction pressure. The amount of the catalyst is generally in a range of from 0.0001 to 30% by weight, preferably 0.005 to 10% by weight, more preferably 0.001 to 1% by weight, based on the total weight of the starting material.

In the present invention, the catalyst used in the first continuous multi-stage distillation column and the catalyst used in the second continuous multi-stage distillation column may be the same or different, but are preferably the same. More preferably, the same catalyst is used in both columns, this catalyst being one that dissolves in the reaction liquid in both columns. In this case, the catalyst dissolved in the high boiling point reaction mixture in the first continuous multi-stage distillation column is generally withdrawn from the lower portion of the first distillation column together with the alkyl aryl carbonate and so on, and fed into the second continuous multi-stage distillation column as is; this is a preferable embodiment. If necessary, the catalyst can be newly added into the second continuous multi-stage distillation column.

The reaction times for the transesterification reactions carried out in the present invention are considered to equate to the average residence times of the reaction liquids in the first continuous multi-stage distillation column and the second continuous multi-stage distillation column. Each of these reaction times varies depending on the form of the internal in the distillation column and the number of stages, the amount of the starting material fed into the column, the type and amount of the catalyst, the reaction conditions, and so on. The reaction time in each of the first continuous multi-stage distillation column and the second continuous multi-stage distillation column is generally in a range of from 0.01 to 10 hours, preferably 0.05 to 5 hours, more preferably 0.1 to 3 hours.

The reaction temperature in the first continuous multi-stage distillation column varies depending on the type of the starting material compounds used, and the type and amount of the catalyst. This reaction temperature is generally in a range of from 100 to 350° C. It is preferable to increase the reaction temperature so as to increase the reaction rate. However, if the reaction temperature is too high, then side reactions become liable to occur, for example production of by-products such as an alkyl aryl ether increases, which is undesirable. For this reason, the reaction temperature in the first continuous multi-stage distillation column is preferably in a range of from 130 to 280° C., more preferably 150 to 260° C., yet more preferably 180 to 250° C.

The reaction temperature in the second continuous multi-stage distillation column varies depending on the type of the starting material compounds used, and the type and amount of the catalyst. This reaction temperature is generally in a range of from 100 to 350° C. It is preferable to increase the reaction temperature so as to increase the reaction rate. However, if the reaction temperature is too high, then side reactions become liable to occur, for example production of by-products such as an alkyl aryl ether, and Fries rearrangement products of the starting material compounds and the produced alkyl aryl carbonate and diaryl carbonate, and derivatives thereof increases, which is undesirable. For this reason, the reaction temperature in the second continuous multi-stage distillation column is preferably in a range of from 130 to 280° C., more preferably 150 to 260° C., yet more preferably 180 to 250° C.

Moreover, the reaction pressure in the first continuous multi-stage distillation column varies depending on the type of the starting material compounds used and the composition of the starting material, the reaction temperature, and so on. The first continuous multi-stage distillation column may be at any of a reduced pressure, normal pressure, or an applied pressure. The pressure at the top of the column is generally in a range of from 0.1 to $2 \times 10^7$ Pa, preferably $10^5$ to $10^7$ Pa, more preferably $2 \times 10^5$ to $5 \times 10^6$ Pa.

The reaction pressure in the second continuous multi-stage distillation column varies depending on the type of the starting material compounds used and the composition of the starting material, the reaction temperature, and so on. The second continuous multi-stage distillation column may be at any of a reduced pressure, normal pressure, or an applied pressure. The pressure at the top of the column is generally in a range of from 0.1 to $2 \times 10^7$ Pa, preferably $10^3$ to $10^6$ Pa, more preferably $5 \times 10^3$ to $10^5$ Pa.

Note that the first continuous multi-stage distillation column may comprise two or more of the distillation column. In this case, two or more of the distillation column may be connected in series or in parallel. Two or more of the distillation column may also be connected in combination of in series and in parallel.

Moreover, the second continuous multi-stage distillation column may comprise two or more of the distillation column. In this case, two or more of the distillation column may be connected in series or in parallel. Two or more of the distillation column may also be connected in combination of in series and in parallel.

The material constituting each of the first continuous multi-stage distillation column and the second continuous multi-stage distillation column used in the present invention is generally a metallic material such as carbon steel or stainless steel. In terms of the quality of the aromatic carbonates produced, stainless steel is preferable.

Hereinbelow, the present invention will be described in more detail with reference to the following Examples, but the present invention is not limited to the following Examples.

EXAMPLES

Following is a more detailed description of the present invention with reference to Examples. However, the present invention is not limited to the following Examples.

The halogen content was measured by means of an ion chromatography method.

Example 1

<First Continuous Multi-Stage Distillation Column 101>

A continuous multi-stage distillation column as shown in FIG. 1 having $L_1=3300$ cm, $D_1=500$ cm, $L_1/D_1=6.6$, $n_1=80$, $D_1/d_{11}=17$, and $D_1/d_{12}=9$ was used. In this Example, the sieve tray having the cross-sectional area per hole being approximately 1.5 cm² and the number of holes being approximately 250/m² were used as the internal.

<Second Continuous Multi-Stage Distillation Column 201>

A continuous multi-stage distillation column as shown in FIG. 2 having $L_2=3100$ cm, $D_2=500$ cm, $L_2/D_2=6.2$, $n_2=30$, $D_2/d_{21}=3.85$, and $D_2/d_{22}=11.1$ was used. In this Example, as the internal, two sets of Mellapak (total number of stages 11) were installed in the upper portion, and the sieve tray having the cross-sectional area per hole being approximately 1.3 cm² and the number of holes being approximately 250/m² were used in the lower portion.

<Reactive Distillation>

Figure 3:
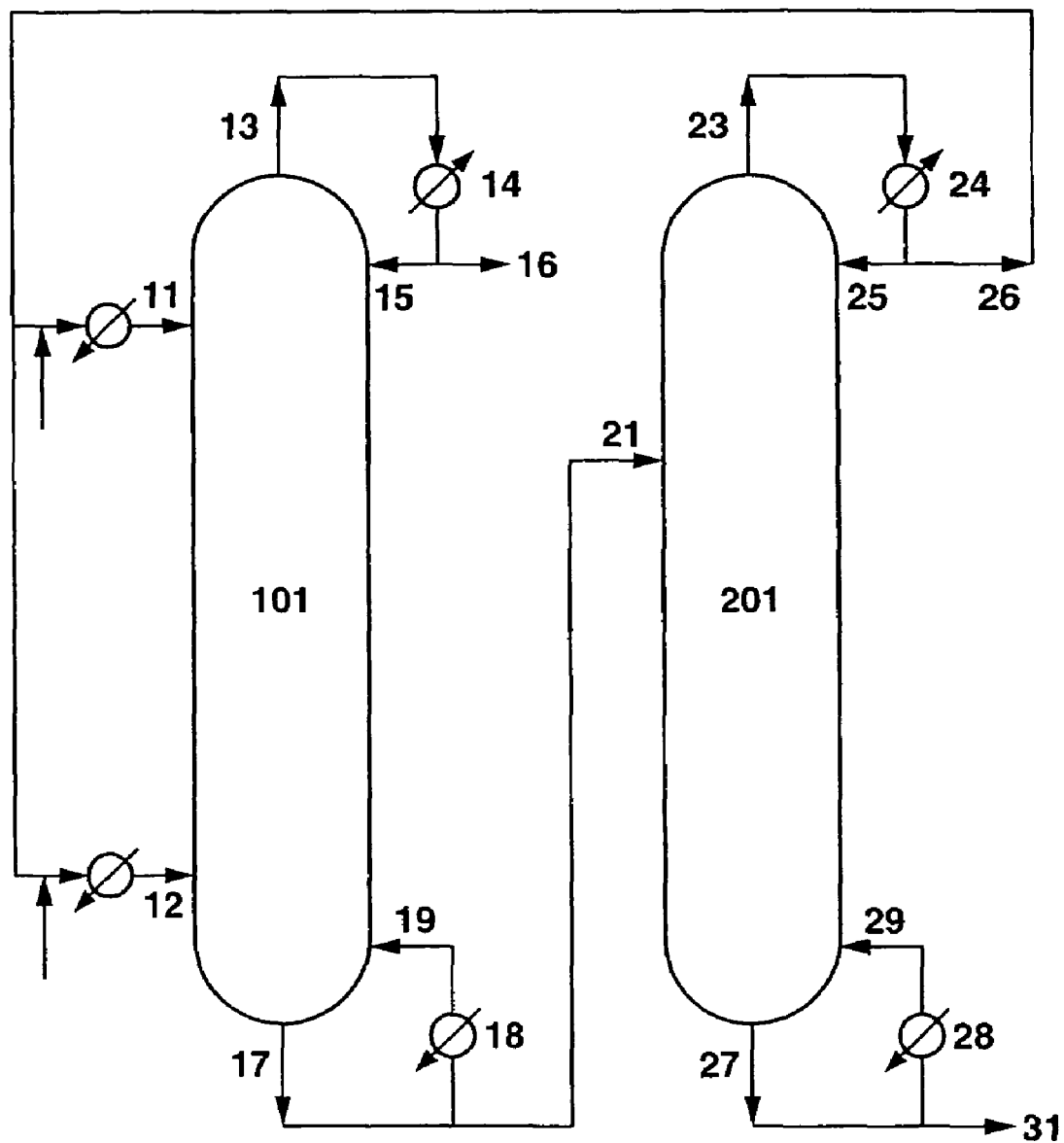
FIG. 3 is a schematic view of an apparatus suitable for carrying out the present invention.

Diphenyl carbonate was produced by carrying out reactive distillation using a apparatus in which the first continuous multi-stage distillation column 101 and the second continuous multi-stage distillation column 201 were connected together as shown in FIG. 3.

A starting material 1 containing phenol and dimethyl carbonate in a weight ratio of phenol/dimethyl carbonate=1.9 was introduced continuously in a liquid form at a flow rate of 50 ton/hr from an upper inlet 11 of the first continuous multi-stage distillation column 101. On the other hand, a starting material 2 containing dimethyl carbonate and phenol in a weight ratio of dimethyl carbonate/phenol=3.6 was introduced continuously in a gaseous form at a flow rate of 50 ton/hr from a lower inlet 12 of the first continuous multi-stage distillation column 101. The molar ratio for the starting materials introduced into the first continuous multi-stage distillation column 101 was dimethyl carbonate/phenol=1.35. The starting materials substantially did not contain halogens (outside the detection limit for the ion chromatography, i.e. 1 ppb or less). Pb(OPh)$_2$ as a catalyst was introduced from the upper inlet 11 of the first continuous multi-stage distillation column 101 such that a concentration thereof in the reaction liquid was approximately 100 ppm. Reactive distillation was carried out continuously under conditions of a temperature at the bottom of the first continuous multi-stage distillation column 101 being 225° C. and a pressure at the top of the column being $7 \times 10^5$ Pa. A first column low boiling point reaction mixture containing methanol, dimethyl carbonate, phenol and so on was continuously withdrawn in a gaseous form from the top 13 of the first column, was passed through a heat exchanger 14, and was withdrawn at a flow rate of 34 ton/hr from an outlet 16. On the other hand, a first column high boiling point reaction mixture containing methyl phenyl carbonate, dimethyl carbonate, phenol, diphenyl carbonate, the catalyst and so on was continuously withdrawn in a liquid form from the bottom 17 of the first column.

A stable steady state was attained after 24 hours. The first column high boiling point reaction mixture was then fed continuously into the second continuous multi-stage distillation column 201 at a flow rate of 66 ton/hr from a starting material inlet 21 installed between the Mellapak and the sieve tray. The liquid fed into the second continuous multi-stage distillation column 201 contained 18.2% by weight of methyl phenyl carbonate and 0.8% by weight of diphenyl carbonate. Reactive distillation was carried out continuously under conditions of a temperature at the bottom of the second continuous multi-stage distillation column 201 being 210° C., a pressure at the top of the column being $3 \times 10^4$ Pa, and a reflux ratio being 0.3. It was possible to attain stable steady state operation after 24 hours. A second column low boiling point reaction mixture containing 35% by weight of dimethyl carbonate and 56% by weight of phenol was continuously withdrawn from the top 23 of the second column, the flow rate at an outlet 26 being 55.6 ton/hr. The second column low boiling point reaction mixture was continuously fed into the first continuous multi-stage distillation column 101 from the inlet 11 and/or the inlet 12. At this time, the amounts of fresh dimethyl carbonate and phenol newly fed into the first continuous multi-stage distillation column 101 were adjusted so as to maintain the above-mentioned compositions and amounts of the starting material 1 and the starting material 2, taking into consideration the composition and amount of the second column low boiling point reaction mixture.

A second column high boiling point reaction mixture containing 38.4% by weight of methyl phenyl carbonate and 55.6% by weight of diphenyl carbonate was continuously withdrawn from the bottom 27 of the second column. It was found that the amount of diphenyl carbonate produced per hour was 5.74 tons. The selectivity for the diphenyl carbonate based on the phenol reacted was 98%.

Prolonged continuous operation was carried out under these conditions. The amounts of diphenyl carbonate produced per hour at 500 hours, 2000 hours, 4000 hours, 5000 hours, and 6000 hours after attaining stable state (excluding the diphenyl carbonate contained in the starting material) were 5.74 tons, 5.75 tons, 5.74 tons, 5.74 tons, and 5.75 tons respectively, and the selectivities were 98%, 98%, 98%, 98%, and 98% respectively, and hence the operation was very stable. Moreover, the aromatic carbonates produced substantially did not contain halogens (1 ppb or less).

Example 2

Reactive distillation was carried out under the following conditions using the same apparatus as in Example 1.

A starting material 1 containing phenol and dimethyl carbonate in a weight ratio of phenol/dimethyl carbonate=1.1 was introduced continuously in a liquid form at a flow rate of 40 ton/hr from the upper inlet 11 of the first continuous multi-stage distillation column 101. On the other hand, a starting material 2 containing dimethyl carbonate and phenol in a weight ratio of dimethyl carbonate/phenol=3.9 was introduced continuously in a gaseous form at a flow rate of 43 ton/hr from the lower inlet 12 of the first continuous multi-stage distillation column 101. The molar ratio for the starting materials introduced into the first continuous multi-stage distillation column 101 was dimethyl carbonate/phenol=1.87. The starting materials substantially did not contain halogens (outside the detection limit for the ion chromatography, i.e. 1 ppb or less). Pb(OPh)$_2$ as a catalyst was introduced from the upper inlet 11 of the first continuous multi-stage distillation column 101 such that a concentration thereof in the reaction liquid was approximately 250 ppm. Reactive distillation was carried out continuously under conditions of a temperature at the bottom of the first continuous multi-stage distillation column 101 being 235° C. and a pressure at the top of the column being $9 \times 10^5$ Pa. A first column low boiling point reaction mixture containing methanol, dimethyl carbonate, phenol and so on was continuously withdrawn in a gaseous form from the top 13 of the first column, was passed through a heat exchanger 14, and was withdrawn at a flow rate of 43 ton/hr from the outlet 16. On the other hand, a first column high boiling point reaction mixture containing methyl phenyl carbonate, dimethyl carbonate, phenol, diphenyl carbonate, the catalyst and so on was continuously withdrawn in a liquid form from the bottom 17 of the first column.

A stable steady state was attained after 24 hours. The first column high boiling point reaction mixture was then fed continuously into the second continuous multi-stage distillation column 201 at a flow rate of 40 ton/hr from the starting material inlet 21 installed between the Mellapak and the sieve tray. The liquid fed into the second continuous multi-stage distillation column 201 contained 20.7% by weight of methyl phenyl carbonate and 1.0% by weight of diphenyl carbonate. Reactive distillation was carried out continuously under conditions of a temperature at the bottom of the second continuous multi-stage distillation column 201 being 205° C., a pressure at the top of the column being $2 \times 10^4$ Pa, and a reflux ratio being 0.5. It was possible to attain stable steady state operation after 24 hours. A second column low boiling point reaction mixture was continuously withdrawn from the top 23 of the second column, the flow rate at the outlet 26 being 33.3 ton/hr.

The second column low boiling point reaction mixture was continuously fed into the first continuous multi-stage distillation column 101 from the inlet 11 and/or the inlet 12. At this time, the amounts of fresh dimethyl carbonate and phenol newly fed into the first continuous multi-stage distillation column 101 were adjusted so as to maintain the above-mentioned compositions and amounts of the starting material 1 and the starting material 2, taking into consideration the composition and amount of the second column low boiling point reaction mixture.

A second column high boiling point reaction mixture containing 35.5% by weight of methyl phenyl carbonate and 61.2% by weight of diphenyl carbonate was continuously withdrawn from the bottom 27 of the second column. It was found that the amount of diphenyl carbonate produced per hour was 4.1 tons. The selectivity for the diphenyl carbonate based on the phenol reacted was 97%.

Prolonged continuous operation was carried out under these conditions. The amounts of diphenyl carbonate produced per hour at 500 hours, 1000 hours, and 2000 hours after attaining stable steady state were 4.1 tons, 4.1 tons, and 4.1 tons respectively, and the selectivities based on the reacted phenol were 97%, 97%, and 97% respectively, and hence the operation was very stable. Moreover, the aromatic carbonates produced substantially did not contain halogens (1 ppb or less).

Example 3

Reactive distillation was carried out under the following conditions using the same apparatus as in Example 1 except that the cross-sectional area per hole of each of the sieve trays in the second continuous multi-stage distillation column 201 was made to be approximately 1.8 cm$^2$.

A starting material 1 containing phenol and dimethyl carbonate in a weight ratio of phenol/dimethyl carbonate=1.7 was introduced continuously in a liquid form at a flow rate of 86 ton/hr from the upper inlet 11 of the first continuous multi-stage distillation column 101. On the other hand, a starting material 2 containing dimethyl carbonate and phenol in a weight ratio of dimethyl carbonate/phenol=3.5 was introduced continuously in a gaseous form at a flow rate of 90 ton/hr from the lower inlet 12 of the first continuous multi-stage distillation column 101. The molar ratio for the starting materials introduced into the first continuous multi-stage distillation column 101 was dimethyl carbonate/phenol=1.44. The starting materials substantially did not contain halogens (outside the detection limit for the ion chromatography, i.e. 1 ppb or less). $Pb(OPh)_2$ as a catalyst was introduced from the upper inlet 11 of the first continuous multi-stage distillation column 101 such that a concentration thereof in the reaction liquid was approximately 150 ppm. Reactive distillation was carried out continuously under conditions of a temperature at the bottom of the first continuous multi-stage distillation column 101 being 220° C. and a pressure at the top of the column being $8\times10^5$ Pa. A first column low boiling point reaction mixture containing methanol, dimethyl carbonate, phenol and so on was continuously withdrawn in a gaseous form from the top 13 of the first column, was passed through a heat exchanger 14, and was withdrawn at a flow rate of 82 ton/hr from the outlet 16. On the other hand, a first column high boiling point reaction mixture containing methyl phenyl carbonate, dimethyl carbonate, phenol, diphenyl carbonate, the catalyst and so on was continuously withdrawn in a liquid form from the bottom 17 of the first column.

A stable steady state was attained after 24 hours. The first column high boiling point reaction mixture was then fed continuously into the second continuous multi-stage distillation column 201 at a flow rate of 94 ton/hr from the starting material inlet 21 installed between the Mellapak and the sieve tray. The liquid fed into the second continuous multi-stage distillation column 201 contained 16.0% by weight of methyl phenyl carbonate and 0.5% by weight of diphenyl carbonate. Reactive distillation was carried out continuously under conditions of a temperature at the bottom of the second continuous multi-stage distillation column 201 being 215° C., a pressure at the top of the column being $2.5\times10^4$ Pa, and a reflux ratio being 0.4. It was possible to attain stable steady state operation after 24 hours. A second column low boiling point reaction mixture was continuously withdrawn from the top 23 of the second column, the flow rate at the outlet 26 being 81.7 ton/hr. The second column low boiling point reaction mixture was continuously fed into the first continuous multi-stage distillation column 101 from the inlet 11. At this time, the amounts of fresh dimethyl carbonate and phenol newly fed into the first continuous multi-stage distillation column 101 were adjusted so as to maintain the above-mentioned compositions and amounts of the starting material 1 and the starting material 2, taking into consideration the composition and amount of the second column low boiling point reaction mixture.

A second column high boiling point reaction mixture containing 35.5% by weight of methyl phenyl carbonate and 59.5% by weight of diphenyl carbonate was continuously withdrawn from the bottom 27 of the second column. It was found that the amount of diphenyl carbonate produced per hour was 7.32 tons. The selectivity for the diphenyl carbonate based on the phenol reacted was 98%.

Prolonged continuous operation was carried out under these conditions. The amounts of diphenyl carbonate produced per hour at 500 hours, 1000 hours, and 2000 hours after attaining stable steady state were 7.32 tons, 7.33 tons, and 7.33 tons respectively, and the selectivities based on the reacted phenol were 98%, 98%, and 98% respectively, and hence the operation was very stable. Moreover, the aromatic carbonates produced substantially did not contain halogens (1 ppb or less).

INDUSTRIAL APPLICABILITY

The present invention is suitable as a specific process that enables aromatic carbonates containing diaryl carbonate as a main product to be produced with high selectivity and high productivity stably for a prolonged period of time on an industrial scale of not less than 1 ton per hour using two continuous multi-stage distillation columns from a dialkyl carbonate and an aromatic monohydroxy compound.

We claim:

1. A process for the production of an aromatic carbonate containing a diaryl carbonate as a main product from a dialkyl carbonate and an aromatic monohydroxy compound as a starting material, which comprises the steps of:
(i) continuously feeding said starting material into a first continuous multi-stage distillation column in which a catalyst is present;
(ii) carrying out the reaction in said first column to produce an alcohol and an alkyl aryl carbonate;
(iii) continuously withdrawing a first column low boiling point reaction mixture containing a produced alcohol from an upper portion of said first column in a gaseous form while continuously withdrawing a first column high boiling point reaction mixture containing an alkyl aryl carbonate from a lower portion of said first column in a liquid form;
(iv) continuously feeding said first column high boiling point reaction mixture into a second continuous multi-stage distillation column in which a catalyst is present and which is connected to said first column while carrying out the reaction in said second column to produce a dialkyl carbonate and a diaryl carbonate;
(v) continuously withdrawing a second column low boiling point reaction mixture containing said produced dialkyl carbonate from an upper portion of said second column in a gaseous form while continuously withdrawing a second column high boiling point reaction mixture containing said produced diaryl carbonate from a lower portion of said second column in a liquid form; wherein
(a) a molar ratio of the dialkyl carbonate to the aromatic monohydroxy compound in said starting material which is fed continuously into said first continuous multi-stage distillation column is in a range of from 0.1 to 10;
(b) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \tag{1}$$

(2) said inside diameter $D_1$ (cm) of the column satisfies the following formula (2), $$100 \leq D_1 \leq 2000 \tag{2}$$

(3) a ratio of said length $L_1$ (cm) to said inside diameter $D_1$ (cm) of the column satisfies the following formula (3), $$2 \leq L_1/D_1 \leq 40 \tag{3}$$

(4) said number of stages $n_1$ satisfies the following formula (4), $$20 \leq n_1 \leq 120 \tag{4}$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \tag{5, and}$$

(6) a ratio of said inside diameter $D_1$ (cm) of the column to said inside diameter $d_{12}$ (cm) of the liquid outlet satisfies the following formula (6), $$3 \leq D_1/d_{12} \leq 20 \tag{6}$$

(c) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \tag{7}$$

(2) said inside diameter $D_2$ (cm) of the column satisfies the following formula (8), $$100 \leq D_2 \leq 2000 \tag{8}$$

(3) a ratio of the length $L_2$ (cm) to said inside diameter $D_2$ (cm) of the column satisfies the following formula (9), $$2 \leq L_2/D_2 \leq 40 \tag{9}$$

(4) said number of stages $n_2$ satisfies the following formula (10), $$10 \leq n_2 \leq 80 \tag{10}$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \tag{11, and}$$

(6) a ratio of said inside diameter $D_2$ (cm) of the column to said inside diameter $d_{22}$ (cm) of the liquid outlet satisfies the following formula (12), $$5 \leq D_2/d_{22} \leq 30 \tag{12}$$

2. The process according to claim 1, wherein distillation is carried out simultaneously in said step (ii) and said step (iv).

3. The process according to claim 1, wherein an amount of said diaryl carbonate produced is not less than 1 ton per hour.

4. In a process for the production of an aromatic carbonate containing a diaryl carbonate as a main product in which the aromatic carbonate containing the diaryl carbonate as the main product are produced continuously by taking a mixture of a dialkyl carbonate and an aromatic monohydroxy compound as a starting material, continuously feeding the starting material into a first continuous multi-stage distillation column in which a catalyst is present, carrying out the reaction and the distillation simultaneously said the first column, continuously withdrawing a first column low boiling point reaction mixture containing a produced alcohol from an upper portion of said first column in a gaseous form, continuously withdrawing a first column high boiling point reaction mixture containing a produced alkyl aryl carbonate from a lower portion of said first column in a liquid form, continuously feeding the first column high boiling point reaction mixture into a second continuous multi-stage distillation column in which a catalyst is present, carrying out the reaction and the distillation simultaneously in said second column, continuously withdrawing a second column low boiling point reaction mixture containing a produced dialkyl carbonate from an upper portion of said second column in a gaseous form, continuously withdrawing a second column high boiling point reaction mixture containing a produced diaryl carbonate from a lower portion of said second column in a liquid form while continuously feeding the second column low boiling point reaction mixture containing the dialkyl carbonate into the first continuous multi-stage distillation column, the improvement in which:

(a) a molar ratio of the dialkyl carbonate to the aromatic monohydroxy compound in said starting material which is fed continuously into said first continuous multi-stage distillation column is in a range of from 0.1 to 10;

(b) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \tag{1}$$

(2) said inside diameter $D_1$ (cm) of the column satisfies the following formula (2), $$100 \leq D_1 \leq 2000 \tag{2}$$

(3) a ratio of said length $L_1$ (cm) to said inside diameter $D_1$ (cm) of the column satisfies the following formula (3), $$2 \leq L_1/D_1 \leq 40 \tag{3}$$

(4) said number of stages $n_1$ satisfies the following formula (4), $$20 \leq n_1 \leq 120 \tag{4}$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \tag{5, and}$$

(6) a ratio of said inside diameter $D_1$ (cm) of the column to said inside diameter $d_{12}$ (cm) of the liquid outlet satisfies the following formula (6), $$3 \leq D_1/d_{12} \leq 20 \qquad (6);$$

(c) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \qquad (7),$$

(2) said inside diameter $D_2$ (cm) of the column satisfies the following formula (8), $$100 \leq D_2 \leq 2000 \qquad (8),$$

(3) a ratio of the length $L_2$ (cm) to said inside diameter $D_2$ (cm) of the column satisfies the following formula (9), $$2 \leq L_2/D_2 \leq 40 \qquad (9),$$

(4) said number of stages $n_2$ satisfies the following formula (10), $$10 \leq n_2 \leq 80 \qquad (10),$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \qquad (11), \text{ and}$$

(6) a ratio of said inside diameter $D_2$ (cm) of the column to said inside diameter $d_{22}$ (cm) of the liquid outlet satisfies the following formula (12), $$5 \leq D_2/d_{22} \leq 30 \qquad (12).$$

5. The process according to claim 4, wherein an amount produced of the diaryl carbonate is not less than 1 ton per hour.

6. The process according to claim 1, wherein $d_{11}$ and $d_{12}$ satisfy the following formula (13), and $d_{21}$ and $d_{22}$ satisfy the following formula (14)

$$1 \leq d_{12}/d_{11} \leq 5 \qquad (13)$$

$$1 \leq d_{21}/d_{22} \leq 6 \qquad (14).$$

7. The process according to claim 1, wherein $L_1$, $D_1$, $L_1/D_1$, $n_1$, $D_1/d_{11}$, and $D_1/d_{12}$ for said first continuous multi-stage distillation column satisfy the following formulae: $2000 \leq L_1 \leq 6000$, $150 \leq D_1 \leq 1000$, $3 \leq L_1/D_1 \leq 30$, $30 \leq n_1 \leq 100$, $8 \leq D_1/d_{11} \leq 25$, and $5 \leq D_1/d_{12} \leq 18$, respectively, and $L_2$, $D_2$, $L_2/D_2$, $n_2$, $D_2/d_{21}$, and $D_2/d_{22}$ for said second continuous multi-stage distillation column satisfy the following formulae: $2000 \leq L_2 \leq 6000$, $150 \leq D_2 \leq 1000$, $3 \leq L_2/D_2 \leq 30$, $15 \leq n_2 \leq 60$, $2.5 \leq D_2/d_{21} \leq 12$, and $7 \leq D_2/d_{22} \leq 25$, respectively.

8. The process according to claim 1, wherein, $L_1$, $D_1$, $L_1/D_1$, $n_1$, $D_1/d_{11}$, and $D_1/d_{12}$ for said first continuous multi-stage distillation column satisfy the following formulae: $2500 \leq L_1 \leq 5000$, $200 \leq D_1 \leq 800$, $5 \leq L_1/D_1 \leq 15$, $40 \leq n_1 \leq 90$, $10 \leq D_1/d_{11} \leq 25$, and $7 \leq D_1/d_{12} \leq 15$, respectively, and $L_2$, $D_2$, $L_2/D_2$, $n_2$, $D_2/d_{21}$, and $D_2/d_{22}$ for said second continuous multi-stage distillation column satisfy the following formulae: $2500 \leq L_2 \leq 5000$, $200 \leq D_2 \leq 800$, $5 \leq L_2/D_2 \leq 15$, $20 \leq n_2 \leq 50$, $3 \leq D_2/d_{21} \leq 10$, and $9 \leq D_2/d_{22} \leq 20$, respectively.

9. The process according to claim 1, wherein each of said first continuous multi-stage distillation column and said second continuous multi-stage distillation column is a distillation column having a tray and/or a packing as the internal.

10. The process according to claim 9, wherein said first continuous multi-stage distillation column is a plate-type distillation column having the tray as the internal, and said second continuous multi-stage distillation column is a distillation column having both the packing and the tray as the internal.

11. The process according to claim 9, wherein each of the trays in said first continuous multi-stage distillation column and said second continuous multi-stage distillation column is a sieve tray having a sieve portion and a down corner portion.

12. The process according to claim 11, wherein said sieve tray has 100 to 1000 holes/m² in the sieve portion.

13. The process according to claim 11, wherein the cross-sectional area per hole of said sieve tray is in a range of from 0.5 to 5 cm².

14. The process according to claim 9, wherein said second continuous multi-stage distillation column is a distillation column having, as said internal, the packing in an upper portion of the column, and the tray in a lower portion of the column.

15. The process according to claim 1, wherein said packing of said internal in said second continuous multi-stage distillation column is one or more of a structured packing.

16. The process according to claim 15, wherein said structured packing in said second continuous multi-stage distillation column is of at least one selected from the group consisting of Mellapak, Gempak, TECHNO-PAK, FLEXI-PAK, a Sulzer packing, a Goodroll packing and a Glitchgrid.

17. The process according to claim 1, wherein said first continuous multi-stage distillation column comprises two or more of distillation columns.

18. The process according to claim 1, wherein said second continuous multi-stage distillation column comprises two or more of distillation columns.

19. An aromatic carbonate comprising a halogen content of not more than 0.1 ppm, produced by the process according to claim 1.

20. A reactive distillation apparatus comprising a first continuous multi-stage distillation column for carrying out reaction and distillation; and a second continuous multi-stage distillation column for carrying out reaction and distillation, which is connected to said first continuous multi-stage distillation column, comprising:

(a) said first continuous multi-stage distillation column comprises a structure having a pair of end plates above and below a cylindrical trunk portion having a length $L_1$ (cm) and an inside diameter $D_1$ (cm), and having an internal with a number of stages $n_1$ thereinside, and has a gas outlet having an inside diameter $d_{11}$ (cm) at the top of the column or in an upper portion of the column near to the top, a liquid outlet having an inside diameter $d_{12}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_1$ (cm) satisfies the following formula (1), $$1500 \leq L_1 \leq 8000 \qquad (1),$$

(2) said inside diameter $D_1$ (cm) of the column satisfies the following formula (2), $$100 \leq D_1 \leq 2000 \qquad (2),$$

(3) a ratio of said length $L_1$ (cm) to said inside diameter $D_1$ (cm) of the column satisfies the following formula (3), $$2 \leq L_1/D_1 \leq 40 \qquad (3),$$

(4) said number of stages $n_1$ satisfies the following formula (4), $$20 \leq n_1 \leq 120 \qquad (4),$$

(5) a ratio of said inside diameter $D_1$ (cm) of the column to said inside diameter $d_{11}$ (cm) of the gas outlet satisfies the following formula (5), $$5 \leq D_1/d_{11} \leq 30 \qquad (5), \text{ and}$$

(6) a ratio of said inside diameter $D_1$ (cm) of the column to said inside diameter $d_{12}$ (cm) of the liquid outlet satisfies the following formula (6), $$3 \leq D_1/d_{12} \leq 20 \qquad (6);$$

(b) said second continuous multi-stage distillation column comprises a structure having a pair of end plates above and below a cylindrical trunk portion having a length $L_2$ (cm) and an inside diameter $D_2$ (cm), and having an internal with a number of stages $n_2$ thereinside, and has a gas outlet having an inside diameter $d_{21}$ (cm) at the top of the column or in an upper portion of the column near to the top, a liquid outlet having an inside diameter $d_{22}$ (cm) at the bottom of the column or in a lower portion of the column near to the bottom, at least one inlet provided in the upper portion and/or a middle portion of the column below the gas outlet, and at least one inlet provided in the lower portion of the column above the liquid outlet, wherein (1) said length $L_2$ (cm) satisfies the following formula (7), $$1500 \leq L_2 \leq 8000 \qquad (7),$$

(2) said inside diameter $D_2$ (cm) of the column satisfies the following formula (8), $$100 \leq D_2 \leq 2000 \qquad (8),$$

(3) a ratio of the length $L_2$ (cm) to said inside diameter $D_2$ (cm) of the column satisfies the following formula (9), $$2 \leq L_2/D_2 \leq 40 \qquad (9),$$

(4) said number of stages $n_2$ satisfies the following formula (10), $$10 \leq n_2 \leq 80 \qquad (10),$$

(5) a ratio of said inside diameter $D_2$ (cm) of the column to said inside diameter $d_{21}$ (cm) of the gas outlet satisfies the following formula (11), $$2 \leq D_2/d_{21} \leq 15 \qquad (11), \text{ and}$$

(6) a ratio of said inside diameter $D_2$ (cm) of the column to said inside diameter $d_{22}$ (cm) of the liquid outlet satisfies the following formula (12), $$5 \leq D_2/d_{22} \leq 30 \qquad (12).$$

21. The reactive distillation apparatus according to claim 20, wherein $d_{11}$ and $d_{12}$ satisfy the following formula (13), and $d_{21}$ and $d_{22}$ satisfy the following formula (14)

$$1 \leq d_{12}/d_{11} \leq 5 \qquad (13)$$

$$1 \leq d_{21}/d_{22} \leq 6 \qquad (14).$$

22. The reactive distillation apparatus according to claim 20, wherein $L_1$, $D_1$, $L_1/D_1$, $n_1$, $D_1/d_{11}$, and $D_1/d_{12}$ for said first continuous multi-stage distillation column satisfy the following formulae: $2000 \leq L_1 \leq 6000$, $150 \leq D_1 \leq 1000$, $3 \leq L_1/D_1 \leq 30$, $30 \leq n_1 \leq 100$, $8 \leq D_1/d_{11} \leq 25$, and $5 \leq D_1/d_{12} \leq 18$, respectively, and $L_2$, $D_2$, $L_2/D_2$, $n_2$, $D_2/d_{21}$, and $D_2/d_{22}$ for said second continuous multi-stage distillation column satisfy the following formulae: $2000 \leq L_2 \leq 6000$, $150 \leq D_2 \leq 1000$, $3 \leq L_2/D_2 \leq 30$, $15 \leq n_2 \leq 60$, $2.5 \leq D_2/d_{21} \leq 12$, and $7 \leq D_2/d_{22} \leq 25$, respectively.

23. The reactive distillation apparatus according to claim 20, wherein $L_1$, $D_1$, $L_1/D_1$, $n_1$, $D_1/d_{11}$, and $D_1/d_{12}$ for said first continuous multi-stage distillation column satisfy the following formulae: $2500 \leq L_1 \leq 5000$, $200 \leq D_1 \leq 800$, $5 \leq L_1/D_1 \leq 15$, $40 \leq n_1 \leq 90$, $10 \leq D_1/d_{11} \leq 25$, and $7 \leq D_1/d_{12} \leq 15$, respectively, and $L_2$, $D_2$, $L_2/D_2$, $n_2$, $D_2/d_{21}$, and $D_2/d_{22}$ for said second continuous multi-stage distillation column satisfy the following formulae: $2500 \leq L_2 \leq 5000$, $200 \leq D_2 \leq 800$, $5 \leq L_2/D_2 \leq 15$, $20 \leq n_2 \leq 50$, $3 \leq D_2/d_{21} \leq 10$, and $9 \leq D_2/d_{22} \leq 20$, respectively.

24. The reactive distillation apparatus according to claim 20, wherein each of said first continuous multi-stage distillation column and said second continuous multi-stage distillation column is a distillation column having a tray and/or a packing as the internal.

25. The reactive distillation apparatus according to claim 24, wherein said first continuous multi-stage distillation column is a plate-type distillation column having the tray as the internal, and said second continuous multi-stage distillation column is a distillation column having both the packing and the tray as the internal.

26. The reactive distillation apparatus according to claim 24, wherein each of the trays in said first continuous multi-stage distillation column and said second continuous multi-stage distillation column is a sieve tray having a sieve portion and a down comer portion.

27. The reactive distillation apparatus according to claim 26, wherein said sieve tray has 100 to 1000 holes/m$^2$ in the sieve portion.

28. The reactive distillation apparatus according to claim 26, wherein the cross-sectional area per hole of said sieve tray is in a range of from 0.5 to 5 cm$^2$.

29. The process according to claim 24, wherein said second continuous multi-stage distillation column is a distillation column having, as said internal, the packing in an upper portion of the column, and the tray in a lower portion of the column.

30. The reactive distillation apparatus according to claim 24, wherein said packing of said internal in said second continuous multi-stage distillation column is one or more of a structured packing.

31. The reactive distillation apparatus according to claim 30, wherein said structured packing in said second continuous multi-stage distillation column is of at least one selected from the group consisting of Mellapak, Gempak, TECHNO-PAK, FLEXI-PAK, a Sulzer packing, a Goodroll packing and a Glitchgrid.

32. The reactive distillation apparatus according to claim 20, wherein said first continuous multi-stage distillation column comprises two or more of distillation columns.

33. The reactive distillation apparatus according to claim 20, wherein said second continuous multi-stage distillation column comprises two or more of distillation columns.

* * * * *